United States Patent
Coy et al.

(10) Patent No.: US 7,326,685 B2
(45) Date of Patent: Feb. 5, 2008

(54) DIAGNOSTIC OR THERAPEUTIC SOMATOSTATIN OR BOMBESIN ANALOG CONJUGATES AND USES THEREOF

(75) Inventors: David H. Coy, New Orleans, LA (US); Joseph A. Fuselier, New Orleans, LA (US); William A. Murphy, Slidell, LA (US); Lichun Sun, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 224 days.

(21) Appl. No.: 10/490,326

(22) PCT Filed: Sep. 20, 2002

(86) PCT No.: PCT/US02/30143

§ 371 (c)(1),
(2), (4) Date: Aug. 31, 2004

(87) PCT Pub. No.: WO03/028527

PCT Pub. Date: Apr. 10, 2003

(65) Prior Publication Data

US 2005/0070470 A1 Mar. 31, 2005

Related U.S. Application Data

(60) Provisional application No. 60/323,851, filed on Sep. 21, 2001.

(51) Int. Cl.
*A61K 38/00* (2006.01)
*A61K 38/31* (2006.01)
*A61K 38/04* (2006.01)

(52) U.S. Cl. .......................... 514/12; 530/311; 530/327
(58) Field of Classification Search ...................... 514/2
See application file for complete search history.

(56) References Cited

U.S. PATENT DOCUMENTS

| | | | |
|---|---|---|---|
| 4,812,590 A | 3/1989 | Saari | 560/137 |
| 4,904,642 A | 2/1990 | Coy et al. | 514/11 |
| 5,073,541 A | 12/1991 | Taylor et al. | 514/9 |
| 5,411,943 A | 5/1995 | Bogden | 514/16 |
| 5,597,894 A | 1/1997 | Coy et al. | 530/311 |
| 5,620,675 A | 4/1997 | McBride et al. | 424/1.69 |
| 5,633,263 A | 5/1997 | Coy et al. | 530/311 |
| 5,708,135 A | 1/1998 | Coy et al. | 530/311 |
| 5,750,499 A | 5/1998 | Hoeger et al. | 514/9 |
| 5,753,627 A | 5/1998 | Albert et al. | 514/16 |
| 5,770,687 A | 6/1998 | Hornik et al. | 530/311 |
| 6,017,509 A | 1/2000 | Dean et al. | 424/1.69 |
| 6,051,554 A | 4/2000 | Hornik et al. | 514/11 |
| 6,156,725 A | 12/2000 | Mukherjee et al. | 514/12 |
| 2002/0094964 A1 | 7/2002 | Chen et al. | |
| 2006/0211607 A1* | 9/2006 | Culler et al. | 514/9 |

FOREIGN PATENT DOCUMENTS

| | | |
|---|---|---|
| WO | WO 91/01144 | 2/1991 |
| WO | WO 96/39161 | 12/1996 |
| WO | WO 97/19954 | 6/1997 |
| WO | WO 98/47524 | 10/1998 |

OTHER PUBLICATIONS

Blower et al., "Iodine-123 Salmon Calcitonin, An Imaging Agent for Calcitonin Receptors: Synthesis, Biodistribution, Metabolism and Dosimetry in Humans," *Eur. J. Nucl. Med.* 25:101-108 (1998).
Chave et al., "Bombesin Family Receptor and Ligand Gene Expression in Human Colorectal Cancer and Normal Mucosa," *Br. J. Cancer* 82:124-130 (2000).
Chen et al., "A Functional Angiotensin II Receptor-GFP Fusion Protein: Evidence for Agonist-Dependent Nuclear Translocation," *Am. J. Physiol. Renal Physiol.* 279:F440-F448 (2000).
Denzler and Reubi, "Expression of Somatostatin Receptors in Peritumoral Veins of Human Tumors," *Cancer* 85:188-198 (1999).
Dubowchik and Walker, "Receptor-Mediated and Enzyme-Dependent Targeting of Cytotoxic Anticancer Drugs," *Pharmacol. Ther.* 83:67-123 (1999).
Duncan and Spreafico, "Polymer Conjugates. Pharmacokinetic Considerations for Design and Development," *Clin. Pharmacokinet.* 27:290-306 (1994).
Evans et al., "Analysis of Somatostatin Receptor Subtype mRNA Expression in Human Breast Cancer," *Br. J. Cancer* 75:798-803 (1997).
Gulec et al., "Antitumor and Antiangiogenic Effects of Somatostatin Receptor-Targeted In Situ Radiation with (111)In-DTPA-JIC 2DL," *J. Surg. Res.* 97:131-137 (2001).
Hornick et al., "Progressive Nuclear Translocation of Somatostatin Analogs," *J. Nucl. Med.* 41:1256-1263 (2000).
Janson et al., "Nuclear Localization of 111In After Intravenous Injection of [111In-DTPA-D-Phe1]-octreotide in Patients with Neuroendocrine Tumors," *J. Nucl. Med.* 41:1514-1518 (2000).
Kahan et al., "Inhibition of Growth of MX-1, MCF-7-MIII and MDA-MB-231 Human Breast Cancer Xenografts after Administration of a Targeted Cytotoxic Analog of Somatostatin, AN-238," *Int. J. Cancer* 82:592-598 (1999).

(Continued)

*Primary Examiner*—Cecilia J. Tsang
*Assistant Examiner*—Maury Audet
(74) *Attorney, Agent, or Firm*—Paul T. Clark; Clark & Elbing, LLP

(57) ABSTRACT

Disclosed are peptide agents and uses thereof that are analogs of biologically active peptides such as somatostatin and bombesin. The compounds of the invention have the general formula X-Y-Z-Q, where X is a cytotoxic agent, therapeutic agent, detectable label or chelating group, and Q is a biologically active peptide. In peptide agents of the invention Y is optionally a hydrophilic polymer or peptide, and Z is a linking peptide bonded to Q at the amino terminus of Q, having two, three, four, or five, amino acid residues selected to link X to Q, while retaining the biological activity of Q. Methods of using these peptide agents in the diagnosis and treatment of diseases are also disclosed.

29 Claims, 2 Drawing Sheets

OTHER PUBLICATIONS

Kratz et al., "Drug-Polymer Conjugates Containing Acid-Cleavable Bonds," *Crit. Rev. Ther. Drug Carrier Syst.* 16:245-288 (1999).

Liu and Edwards, "Bifunctional Chelators for Therapeutic Lanthanide Radiopharmaceuticals," *Bioconjug. Chem.* 12:7-34 (2001).

Lukinius et al., "In Vivo Cellular Distribution and Endocytosis of the Somatostatin Receptor-Ligand Complex," *Acta Oncol* 38:383-387 (1999).

Mariani et al., "Emerging Roles for Radiometabolic Therapy of Tumors Based on Auger Electron Emission," *J. Nucl. Med.* 41:1519-1521 (2000).

Millar et al., "A Novel Mammalian Receptor for the Evolutionarily Conserved Type II GnRH," *Proc. Natl. Sci. USA* 98:9636-9641 (2001).

Monfardini and Veronese, "Stabilization of Substances in Circulation," *Bioconjug. Chem.* 9:418-450 (1998).

Morel, "Internalization and Nuclear Localization of Peptide Hormones," *Biochem. Pharmacol.* 47:63-76 (1994).

Neill et al., "A Gonadotropin-Releasing Hormone (GnRH) Receptor Specific for GnRH II in Primates," *Biochem. Biophys. Res. Commun.* 282:1012-1018 (2001).

Plonowski et al., "Inhibition of Metastatic Renal Cell Carcinomas Expressing Somatostatin Receptors by a Targeted Cytotoxic Analogue of Somatostatin AN-238," *Cancer Res.* 60:2996-3001 (2000).

Raynor et al., "Cloned Somatostatin Receptors: Identification of Subtype-Selective Peptides and Demonstration of High Affinity Binding of Linear Peptides," *Mol. Pharmacol.* 43:844 (1993).

Rypacek et al., "The Renal Excretion and Retention of Macromolecules: The Chemical Structure Effect," *Pflugers Arch.* 392:211-217 (1982).

Sastry, "Biological Effects of the Auger Emitter Iodine-125: A Review. Report No. 1 of AAPM Nuclear Medicine Task Group No. 6," *Med. Phys.* 19:1361-1370 (1992).

Schaer et al., "Somatostatin Receptor Subtypes $sst_1$, $sst_2$, $sst_3$ and $sst_5$ Expression in Human Pituitary, Gastroentero-Pancreatic and Mammary Tumors: Comparison of mRNA Analysis with Receptor Autoradiography," *Int. J. Cancer* 70:530-537 (1997).

Takahashi et al., "Expression of Urotensin II and Urotensin II Receptor mRNAs in Various Human Tumor Cell Lines and Secretion of Urotensin II-Like Immunoreactivity by SW-13 Adrenocortical Carcinoma Cells," *Peptides* 22:1175-1179 (2001).

Vigroux et al., "Cyclization-Activated Prodrugs: N-(Substituted 2-Hydroxyphenyl and 2-Hydroxypropyl)Carbamates Based on Ring-Opened Derivatives of Active Benzoxazolones and Oxazolidinones as Mutual Prodrugs of Acetaminophen," *J. Med. Chem.* 38:3983-3994 (1995).

Wheldon et al., "The Curability of Tumours of Differing Size by Targeted Radiotherapy Using $^{131}$I or $^{90}$Y," *Radiother. Oncol.* 21:91-99 (1991).

Woltering et al., "Somatostatin Analogues Inhibit Angiogenesis in the Chick Chorioallantoic Membrane," *J. Surg Res.* 50:251 (1991).

Yamaoka et al., "Distribution and Tissue Uptake of Poly(Ethylene Glycol) with Different Molecular Weights After Intravenous Administration to Mice," *J. Pharm. Sci.* 83:601-606 (1994).

Yamaoka et al., "Comparison of Body Distribution of Poly(Vinyl Alcohol) with Other Water-Soluble Polymers after Intravenous Administration," *J. Pharm. Pharmacol.* 47:479-486 (1995).

\* cited by examiner

US 7,326,685 B2

DIAGNOSTIC OR THERAPEUTIC SOMATOSTATIN OR BOMBESIN ANALOG CONJUGATES AND USES THEREOF

CROSS-REFERENCE TO RELATED APPLICATIONS

This application is the National Stage of International Application No. PCT/US02/30143, filed Sep. 20, 2002, which was published in English under PCT Article 21(2), which claims benefit of U.S. Provisional Application No. 60/323,851, filed Sep. 21, 2001, each of which is hereby incorporated by reference.

FIELD OF THE INVENTION

The invention relates to somatostatin and bombesin analogs and uses thereof for targeting compounds useful in the detection, diagnosis or treatment of disease.

BACKGROUND

The toxic side effects of many therapies, including standard treatments for cancers, effectively limit the amount of agent that may be administered to a patient. Additionally, many agents cause organ-specific toxicities, further limiting the dose that may be delivered to the target tissue. For instance, the cardiotoxicity of many anthracycline family members reduces the maximum therapeutic dose available for this group of chemotherapeutic agents. Targeted drug delivery of various detectable or therapeutic agents can lower toxicity in normal tissue and increase the efficacy of treatment by allowing concentrated localized effects on specific tissues.

Somatostatin, bombesin, or other biologically active peptide analogs have been used to detect tumor cells over expressing receptors specific for the peptides (see for example Denzler and Reubi, *Cancer* 85(1):188-198, 1999). Somatostatin, bombesin, and many other biologically active peptide agonist analogs are rapidly internalized after binding to their receptors (Lukinius et al, *Acta Onc.* 38:383-387, 1999; Morel, *Biochem. Pharmacol.* 47(1):63-76, 1994). This internalization of the peptide analogs may result in translocation to the cell nucleus (Chen et al., *Am. J. Physiol. Renal Physiol.* 279:F440-F448, 2000; Hornick et al., *J. Nucl. Med.* 41(7):1256-1263, 2000; Janson et al., *J. Nucl. Med.* 41(9): 1514-1518, 2000).

Somatostatin analogs bind particular somatostatin receptor subtypes that are present on the surface of specific normal or diseased tissues. Somatostatin receptors are up-regulated in specific diseased tissues including inflammatory bowel diseases, rheumatoid arthritis, a variety of tumor types, and blood vessels supplying many tumors, often in a subtype-specific manner. (Denzler and Reubi, *Cancer,* 85:188-198, 1999; Plonowski et al., *Cancer Res.* 60(11): 2996-3001, 2000; Kahan et al., *Int. J. Cancer* 82(4):592-598, 1999; Gulec et al., *Surg. Res.* 97(2):131-137, 2001). Similarly, receptors specific for another biologically active peptide, substance P, can be up-regulated in various diseases (Id.). Somatostatin-related urotensin II peptide receptors have been found to be expressed on a number of neural tumors (Takahashi et al., *Peptides* 22:1175-1179, 2001). Receptors for GnRH II ligands/analogs have been located on many peripheral tissues of interest including breast, prostate, and the GI tract (Neill et al., *Biochem. Biophys. Res. Commun.* 282:1012-1019; Millar et al., *Proc. Natl. Acad. Sci. USA* 98:963609641, 2001).

At least five somatostatin receptors subtypes have been characterized, and tumors can express various receptor subtypes (Shaer et al., *Int. J. Cancer* 70:530-537, 1997). Naturally occurring somatostatin and its analogs exhibit differential binding to these receptor subtypes, allowing precise targeting of a peptide analog to specific diseased tissues.

The physical and chemical properties of many compounds such as cytotoxic agents make their conjugation to biologically active peptides problematic. The agent or drug may reduce the specificity of binding or the biological activity of the peptide analog, limiting its effectiveness as a targeting agent. Additionally, therapeutic and cytotoxic agents may have chemical properties that cause reduced solubility and promote accumulation of drug-peptide analogs in certain organs, thus increasing toxicity and reducing efficacy. Effective means are needed to link cytotoxic agents to a targeting agent such as somatostatin, bombesin, or another biologically active peptide and to decrease non-target uptake of the cytotoxic agents, while retaining the activity of each component, thus maximizing therapeutic effects and minimizing toxicity.

Furthermore, while iodinization and astatination (see Vaidyanathan et al., *Nucl. Med. Biol.* 27(4):329-337, 2000) hold great promise for use in imaging and possibly in aiding treatment of diseases associated with increased expression of a factor specific for a biologically active peptide, problems exist with the methods now available for labeling a range of peptide analogs. The use of labeled biologically active peptides has been studied in various systems. Radioactive halogens such as iodine have great potential as tumor imaging and cytotoxic agents. Promising isotopes include $^{125}$I (K. S. Sastry, *Am. Assoc. Phys. Med.* 19:1361-1370, 1992; Mariano, *J. Nucl. Med.* 41(9):1519-1521, 2000), $^{131}$I (Wheldon et al., *Radiother. Oncol.,* 21:91-99, 1991), $^{123}$I (Blower et al., *Eur. J. Nucl. Med.* 25:101-108, 1998; Janson et al, *J. Nuc. Med.* 41(9):1514-1518, 2000; Mariani et al, *J. Nuc. Med.* 41(9):1519-1521, 2000), and $^{124}$I (Glaser et al., *J. Labelled Compd. Radiopharm.* 44(6):465-480, 2001). There are several problems associated with the addition of radioactive iodine atoms to peptides (Bakker et al., *Eur. J. Nucl. Med.* 23(7):775-781, 1996). One is the rapid loss of iodines from L-Tyr residues by specific de-iodination enzymes (Kawai et al., *Nucl. Med. Biol.* 17(4):369-76, 1990). Another problem is the great increase in hydrophobicity produced by addition of iodine to a peptide agent, which is associated with increased accumulation of radioactivity in the liver, interfering with tumor imaging and promoting severe toxicity. A further problem is loss of binding affinity when tyrosines next to the pharmacophore are iodinated. A linker capable of facilitating labeling of a variety of biologically active peptides without deleterious in vivo accumulation is needed.

SUMMARY OF INVENTION

The present invention features biologically active peptides such as somatostatin or bombesin conjugated to chemical compounds through linkers that allow retention of the peptide's biological activity. Such peptide agents are useful for specifically targeting therapeutic agents, cytotoxic agents, or detectable labels to cells, such as cancer cells expressing somatostatin or bombesin receptors.

In a first aspect, the invention features a peptide agent of the formula:

X-Y-Z-Q wherein X is optionally selected from cytotoxic agents, therapeutic agents, detectable labels or chelating groups; Y is a peptide that increases the biodistribution of the peptide agent, a hydrophilic polymer that includes a linker for X, or is omitted; Q is a biologically active peptide such as somatostatin or bombesin, and Z is a linking peptide that, when bonded to Q at the N-terminus or at a compatible side-chain amino group of Q, preserves at least 50% of the biological activity of Q. Z has the formula: A-B-C-E-F (SEQ ID NO: 1), where A is D-Lys, D-Tyr, D-Ser, or L-Ser, or deleted; B is D-Lys or D-Tyr, or is deleted; C is Lys, Ser, hSer, Thr, Nle, Abu, Nva, (2,3, or 4) 3-pyridyl-Ala (Pal), Orn, Dab, Dap, 4-NH$_2$-Phe, D-4-OH-Pro, or L-4-OH-Pro, or is deleted; E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; provided that when A, B, C, and E are Tyr, Tyr, Lys, and Tyr, respectively, F is not Lys; and when A, B, C, and E, are Lys, Tyr, Lys, and Tyr, respectively, E is not Tyr or Lys; and when A and B are deleted, and C and E are Lys and Tyr, respectively, F is not Tyr or Lys.

In a second, related aspect, the invention features a peptide agent having the formula:

X-Y-Z-Q wherein: X is a cytotoxic or therapeutic agent; Y is a peptide that increases the hydrophilic distribution of the peptide agent, a hydrophilic polymer that includes a linker for X, or is omitted; Q is a peptide having biological activity; and Z is a linking peptide that when bonded to Q at the N-terminus or at a compatible side-chain amino group of Q, preserves at least 50% of the biological activity of Q, wherein Z has the formula:

```
    A-B-C-E-F         (SEQ ID NO: 1)
``` where A is D-Lys, D-Tyr, D-Ser, or L-Ser, or is deleted; B is D-Lys or D-Tyr, or is deleted; C is Lys, Ser, hSer, Thr, Nle, Abu, Nva, (2, 3, or 4) 3-pyridyl-Ala (Pal), Orn, Dab, Dap, 4-NH$_2$-Phe, D-4-OH-Pro, or L-4-OH-Pro, or is deleted; E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; provided that when A, B, C, and E are Tyr, Tyr, Lys, and Tyr, respectively, F is not Lys; and when A, B, C, and E are Lys, Tyr, Lys, and Tyr, respectively, E is not Tyr or Lys; and when A and B are deleted, and C and E are Lys and Tyr, respectively, F is not Tyr or Lys. The Z peptide linker may thus be 2, 3, 4, or 5 residues in length.

In one embodiment of the first and second aspects of the invention, X is a cytotoxic agent or cytotoxic agents. Preferably, X is an antimetabolic agent. The cytotoxic agent may be selected from the group consisting of: doxorubicin, methotrexate, camptothecin, homocamptothecins, rhizoxins, dolistatins, paclitaxel, combretastatin, and maytansinoids, or derivatives or analogs thereof. For example, the cytotoxic agent methotrexate may be linked through the linker Z or Y-Z to a peptide analog, forming a peptide agent of the invention. Preferred cytotoxic agents are rhizoxin, rhizoxin-D, camptothecin and its active analogs, homocamptothecin, ansamitocin P-3, dolistatins, epothilones, combretastatins, and combretastatin A-4.

In other preferred embodiments, the linking peptide Z is D-Ser-Nle-D-Ser-D-Ser (SEQ ID NO: 2), D-Ser-Lys-D-Ser-D-Ser (SEQ ID NO: 3), D-Ser-Lys-D-Tyr-D-Tyr (SEQ ID NO: 4), D-Ser-Lys-D-Tyr-D-Ser (SEQ ID NO: 5), D-Ser-Ser-D-Lys-D-Ser (SEQ ID NO: 6), D-Ser-Ser-D-Lys-Ser (SEQ ID NO: 6), D-Ser-Nle-D-Tyr-D-Ser (SEQ ID NO: 7), D-Ser-Pal-D-Tyr-D-Ser (SEQ ID NO: 8), D-Ser-Thr-D-Tyr-D-Ser (SEQ ID NO: 9), Lys-D-Ser-D-Ser (SEQ ID NO: 10), Ser-D-Lys-D-Ser (SEQ ID NO: 11), Ser-D-Lys-Ser (SEQ ID NO: 11), Nle-D-Tyr-D-Ser (SEQ ID NO: 12), Lys-D-Tyr-D-Ser (SEQ ID NO: 13), Pal-D-Lys-D-Ser (SEQ ID NO: 14), Thr-D-Tyr-D-Ser (SEQ ID NO: 15), D-Ser-D-Lys, D-Ser-D-Tyr, D-Lys-D-Lys, D-Lys-D-Tyr, or D-Tyr-D-Lys.

In a third aspect of the invention, the peptide agent has the formula:

X-Y-Z-Q, where X is a chelating group, or is omitted; Y is a peptide that increases the hydrophilic biodistribution of the peptide agent, a hydrophilic polymer that includes a linker for X, or is omitted; Q is a peptide having biological activity; Z is a linking peptide that, when bonded to Q at the N-terminus or at a compatible side-chain amino group of Q, preserves at least 50% of the biological activity of Q. In this aspect of the invention, Z has the formula: C-E-F (SEQ ID NO: 16), where C is Lys, Orn, Dab, Dap, 4-NH$_2$-Phe, Nle, Ser, hSer, Abu, Nva, D-4-OH-Pro, or L-4-OH-Pro, or is deleted; and E and F are each independently selected from the group consisting of: D-Lys, D-Tyr, D-Ser, D-4-OH-Pro, L-4-OH-Pro, 3-iodo-D-Tyr, 3-5 diiodo-D-Tyr, 3-bromo-D-Tyr, 3-5 dibromo-D-Tyr, D-Asn, D-Asp, L-Asp, D-Glu, or L-Glu; and when C and E are Lys and D-Tyr, respectively, F is not D-Tyr or D-Lys.

In alternative embodiments of the third aspect, the peptide agents of the invention are attached to a detectable label directly or indirectly. The detectable label is preferably radioactive, such as radiolabeled iodine, astatine, or bromine bonded to an amino acid residue of the agent. Alternatively, X may be a chelating group and may contain, for example, an isotope of Lu, In, Y, or Sm, or X may be omitted. If X is omitted, Y may be lower acetylated, succinylated, maleinylated or fumarylated.

In multiple embodiments of the third aspect, the invention features a peptide agent in which Z is:

```
    Lys-D-Tyr-D-Ser,        (SEQ ID NO: 13)

Lys-D-Ser-D-Ser,        (SEQ ID NO: 10)

or

Nle-D-Tyr-D-Ser.        (SEQ ID NO: 12)
```

In another embodiment of the third aspect of the invention, Z may be three amino acids in length. Z is preferably the peptide agent of the formula:

```
    C-E-F,                  (SEQ ID NO: 17)
``` where C is selected from the amino acids listed as above, E is D-Tyr and F is D-Ser. Alternatively, Z may be Lys-D-Tyr-D-Ser (SEQ ID NO: 13), Lys-D-Ser-D-Ser (SEQ ID NO: 10), or Nle-D-Tyr-D-Ser (SEQ ID NO: 12).

In another embodiment of the third aspect, the invention features compositions in which Z has the formula:

C-E-F            (SEQ ID NO: 17)

where C is selected from the group consisting of Lys, Orn, Dab, Dap, 4-NH$_2$-Phe, Nle, Ser, hSer, Abu, Nva, D-4-OH-Pro, and L-4-OH-Pro, or is deleted; E is D-Tyr; and F is D-Ser.

In the first, second, and third aspects of the invention, Y may be a peptide sequence that increases the hydrophilic biodistribution of the biologically active peptide conjugate. For example, in a preferred embodiment, Y is of the formula U(V-V)$_n$ (SEQ ID NO: 18), wherein U is D-Pro, L-Pro, D-4-OH-Pro, L-4-OH-Pro, Sarcosine, Lys, Orn, Dab, Dap, 4-NH$_2$-Phe, or (NH$_2$-(CH$_2$)$_m$—COOH), where m=2-10, inclusive, or is deleted; each V is independently selected from the group consisting of: D-Ser, L-Ser, D-Thr, L-Thr, D-Gln, L-Gln, D-Asn, L-Asn, D-4-OH-Pro, or L-4 hydroxy-Pro; and n=1-50, inclusive. In another preferred embodiment, each V is independently D-Ser or L-Ser (SEQ ID NO: 19). In another preferred embodiment, at least one V is a D-amino acid.

In the alternative, Y may be a hydrophilic polymer. For example, Y may be polyethylene glycol, polyvinyl acetate, polyvinyl alcohol, HPMA (N-(2-hydroxypropyl) methacrylamide) or HPMA copolymers, α, β-poly(N-hydroxyethyl)-DL-aspartamide (PHEA), α, β-poly(N-hydroxypropyl)-DL-aspartamide, or polyvinyl acetate.

The biologically active peptide Q is preferably a somatostatin peptide or a bombesin peptide.

In one embodiment of the invention, Q is bombesin and Z has the formula:

E-F where E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln.

The present invention also provides methods of treating or diagnosing a disease comprising administering to a subject suffering from said disease a therapeutically effective amount of the peptide agents of the invention. For example tumors, or their angiogenic vessels, of the lung, breast, brain, eye, prostate, or colon, the corresponding angiogenic blood vessels, or tumors of neuroendocrine origin, for example carcinoid syndrome, may be treated with a peptide agent.

Other features and advantages of the invention will be apparent from the following detailed description and from the claims.

DEFINITIONS

In accordance with the present invention, by "therapeutic agent" is meant any compound that is used in the detection, diagnosis or treatment of human disease. Such compounds may be naturally occurring, modified, or synthetic. Therapeutic agents may promote or inhibit any biological process implicated in a human disease pathway. Preferred disease targets include, but are not limited to, inflammatory bowel disease, rheumatoid arthritis, neoplastic cells or aberrantly proliferating cells, carcinoid syndrome, acromegaly, and angiogenesis. A therapeutic agent may be, for example, antineoplastic, including cytotoxic. Antineoplastic agents may be alkylating agents, antibiotics, antimetabolites, hormonal agonists or antagonists, tubulin inhibitors, topoisomerase I and II inhibitors, or immunomodulators. They may operate through other mechanistic pathways, or antineoplastic agents may be supplementary potentiating agents.

By "cytotoxic agent" is meant any naturally occurring, modified, or synthetic compound that is toxic to tumor cells. Such agents are useful in the treatment of neoplasms, as well as inflammatory diseases, autoimmune disorders, and in the treatment of other symptoms or diseases characterized by cell proliferation or a hyperactive cell population. Cytotoxic agents include, but are not limited to, alkylating agents, antibiotics, antimetabolites, tubulin inhibitors, topoisomerase I and II inhibitors, hormonal agonists or antagonists, or immunomodulators. They may also be cytotoxic when activated by light or infrared (Photofrin, IR dyes; *Nat. Biotechnol.* 19(4):327-331, 2001). They may operate through other mechanistic pathways, or cytoxic agents may also be supplementary potentiating agents.

By "detectable label" is meant any type of label which, when attached to a peptide agent, renders the compound detectable. A detectable label may be toxic or non-toxic, and may have one or more of the following attributes, without restriction: fluorescence (Kiefer et al., WO 9740055), color, toxicity (e.g., radioactivity, e.g., a γ-emitting radionuclide, Auger-emitting radionuclide, β-emitting radionuclide, an α-emitting radionuclide, or a positron-emitting radionuclide), radiosensitivity, or photosensitivity. Although a detectable label may be directly attached to an amino acid residue of an analog of the invention, a detectable label may also be indirectly attached, for example, by being complexed with a chelating group that is attached (e.g., linked via a covalent bond or indirectly linked) to an amino acid residue of an analog. A detectable label may also be indirectly attached to an analog by the ability of the label to be specifically bound by a second molecule. One example of this type of an indirectly attached label is a biotin label that can be specifically bound by the second molecule, streptavidin. The second molecule may also be linked to a moiety that allows neutron capture (e.g., a boron cage as described in, for example, Kahl et al., *Proc. Natl. Acad. Sci. USA* 87:7265-7269, 1990).

A detectable label may also be a metal ion from heavy elements or rare earth ions, such as $Gd^{3+}$, $Fe^{3+}$, $Mn^{3+}$, or $Cr^{2+}$ (see, for example, *Invest. Radiol.* 33(10):752-761, 1998). Preferred radioactive detectable labels are radioactive iodine labels (e.g., $^{122}I$, $^{123}I$, $^{124}I$, $^{125}I$, or $^{131}I$) that are capable of being coupled to each D- or L-Tyr or D- or L-4-amino-Phe residue present in the analogs of the invention. Preferred non-radioactive detectable labels are the many known dyes that are capable of being coupled to NH$_2$-terminal amino acid residues.

Preferred examples of detectable labels that may be toxic to cells include ricin, diptheria toxin, and radioactive detectable labels (e.g., $^{122}I$, $^{123}I$, $^{124}I$, $^{125}I$, $^{131}I$, $^{177}Lu$, $^{64}Cu$, $^{67}Cu$, $^{153}Sm$, $^{166}Ho$, $^{186}Re$, $^{188}Re$, $^{211}At$, $^{212}Bi$, $^{225}Ac$, $^{67}Ga$, $^{68}Ga$, $^{75}Br$, $^{76}Br$, $^{77}Br$, $^{117m}Sn$, $^{47}Sc$, $^{109}Pd$, $^{89}Sr$, $^{159}Gd$, $^{149}Pm$, $^{142}Pr$, $^{111}Ag$, $^{165}Dy$, $^{213}Bi$, $^{111}In$, $^{114m}In$, $^{201}Ti$, $^{195m}Pt$, $^{193}Pt$, $^{86}Y$ and $^{90}Y$). These compounds, and others described herein may be directly or indirectly attached to a biologically active peptide or its analogs. A toxic detectable label may also be a chemotherapeutic agent (e.g., camptothecins, homocamptothecins, 5-fluorouracil or adriamycin), or may be a radiosensitizing agent (e.g., Taxol, gemcitabine, fluoropyrimidine, metronitozil, or the deoxycytidine analog 2',2' difluoro-2'-deoxycytidine (dFdCyd) to which is directly or indirectly attached a somatostatin analog of the present invention.

By "chelating group" is meant any group covalently bound to the peptide agent, that may complex with a detectable label, such as a metal, photosensitizing agent, etc. Chelating groups, for example, include an iminodicarboxylic group or a polyaminopolycarboxylic group. Chelating groups may be attached to a peptide agent of the invention using the methods generally described in Liu et al., *Bioconjugate Chem.* 12(4):653, 2001; Alter et al., U.S. Pat. No. 5,753,627; and PCT Publication No. WO 91/01144; both of which are hereby incorporated by reference). An analog of the invention may be complexed, through its attached chelating agent, to a detectable label, thereby resulting in an analog that is indirectly labeled. Similarly, cytotoxic or therapeutic agents, may also be attached via a chelating group to a peptide agent of the invention.

By "biologically active peptide" is meant any naturally occurring, modified, or synthetic peptide that is involved in a biological process or function. Examples of biologically active peptides include, but are not limited to: hormones, growth factors, neurotransmitters, antigens, antibodies, or fragments thereof, etc. By "peptide" is meant any polypeptide, peptide (including cyclic or branched peptides), or protein comprising two or more amino acids joined to each other by peptide bonds or modified peptide bonds. "Peptide" refers to both short chains, commonly referred to as peptides, oligopeptides, or oligomers, and to longer chains, up to about 100 residues in length. Peptides may contain amino acids other than the 20 gene-encoded amino acids, and linkages other than peptide bonds. "Peptides" include amino acid sequences modified either by natural processes, or by chemical modification techniques which are well known in the art. Modifications may occur anywhere in a polypeptide, including the peptide backbone, the amino acid side-chains, and the amino or carboxyl termini.

The notations used herein for the peptide amino acid residues are those abbreviations commonly used in the art. The less common abbreviations Abu, Ava, β-Ala, hSer, Nle, Nva, Pal, Sar, Dab, and Dap stand for 2-amino-butyric acid, amino valeric acid, beta-aminopropionic acid, homoserine, norleucine, norvaline, (2,3, or 4) 3-pyridyl-Ala, 1,4-diaminobutyric acid, sarcosine, and 1,3-diaminopropionic acid, respectively. In all aspects of the invention, it is noted that when amino acids are not designated as either D- or L-amino acids, the amino acid is either an L-amino acid or could be either a D- or L-amino acid.

By "analog" is meant a molecule that differs from, but is structurally, functionally, and/or chemically related to the reference molecule. The analog may retain the essential properties, functions, or structures of the reference molecule. Most preferably, the analog retains at least one biological function of the reference molecule. Generally, differences are limited so that the structure or sequence of the reference molecule and the analog are similar overall. A peptide analog and its reference peptide may differ in amino acid sequence by one or more substitutions, additions, and/or deletions, in any combination. A substituted or inserted amino acid residue may or may not be one encoded by the genetic code. An analog of a peptide or polypeptide may be naturally occurring such as an allelic variant, or it may be a variant that is not known to occur naturally. Non-naturally occurring analogs of peptides may be made by direct synthesis, by modification, or by mutagenesis techniques.

By "somatostatin peptide" is meant a somatostatin analog having at least one biological activity of native somatostatin; preferably, this activity is the ability to specifically bind to a somatostatin receptor on a somatostatin receptor-bearing cell. Many such analogs having biological activity are known and have been described, for example, in Hornik et al., U.S. Pat. No. 5,770,687; Coy et al., U.S. Pat. No. 5,708,135; Hoeger et al., U.S. Pat. No. 5,750,499; McBride et al., U.S. Pat. No. 5,620,675; Coy et al., U.S. Pat. No. 5,633,263; Coy et al., U.S. Pat. No. 5,597,894; Taylor et al., U.S. Pat. No. 5,073,541; Coy et al., U.S. Pat. No. 4,904,642; Dean, U.S. Pat. No. 6,017,509; Hoffman et al., WO 98/47524; and A. E. Bogden, U.S. Pat. No. 5,411,943, each of which is hereby incorporated by reference.

The term "bombesin peptide" encompasses bombesin peptide analogs having at least one biological activity of native bombesin; preferably, this activity is the ability to specifically bind to one or all of the three known bombesin receptor subtypes on a bombesin receptor-bearing cell. Bombesin analogs include, but are not limited to, peptides selected from the group containing the octapeptide G-Trp-H-I-His-J-K-NHV (SEQ ID NO: 20), wherein G is Gln, Asn, Nle, or Nva; H is Ava, Gly, Leu, Val, Ile, Nle, or Nva; I is β-Ala, 4-aminobutyric acid, Gly, Ala, D-Ala, N-Me-Ala, or N-Me-D-Ala; J is Phe, Tyr, 4-Cloro-Phe, 4-Fluoro-Phe, 4-Bromo-Phe, 4-NO$_2$-Phe, Ala, Gly, Leu, Val, Ile, Nle, or Nva; K is Met, Phe, Tyr, 4-Cloro-Phe, 4-Fluoro-Phe, 4-Bromo-Phe, 4-NO$_2$-Phe, Ala, Gly, Leu, Val, Ile, Nle, or Nva; and N represents an amide or a N-alkylamide and V is H or a lower alkylamide.

By "alkyl" is meant an aliphatic branched or straight chain hydrocarbon group. An alkyl is optionally substituted with one or more substituents which may be the same or different. By "lower alkyl" is meant a branched or straight chain alkyl group having less than 11 carbon atoms, preferably a $C_1$-$C_8$ alkyl. By "lower alkylamide" is meant a lower alkyl group as described above substituted with one or more amide-containing groups.

By "hydrophilic biodistribution" is meant the affinity of the peptide agents of the invention for the bodily fluids of a subject administered the peptide agents (e.g., blood, cerebrospinal fluid, urine, or other bodily fluids), such that the peptide agents distribute throughout the body of the subject, but are rapidly secreted in the urine via the kidney, while avoiding uptake by peripheral organs such as liver, gall bladder, and kidney proximal tubules.

By "hydrophilic polymer" is meant a naturally occurring or synthetic water-soluble polymer optionally modified that alters the biodistribution of a peptide agent of the invention. Examples of such polymers include, but are not limited to poly(ethylene glycol) (PEG), poly(vinyl alcohol) (PVA), dextran, hydroxyelthyl starch, gelatin, PVP, PHPMA, poly α, β[N(2-hydroxyethyl)D,L aspartamide (PHEA), polysuccinamide (PSI), etc. These polymers may be modified by, for example, succinylation (negative charge), partial hydrolysis of PSI (carboxylic groups), or reaction with compounds to add amino- or carboxyl-containing groups, etc. Such optional modifications may increase or change the polymer's hydrophilicity or enable coupling to the peptide or cytotoxic, therapeutic, or chelating segments of a peptide agent of the invention. Such polymers and modifications are known in the art and are described in, for example, Yamoaka et al., *J. Pharmacol. Sci.* 83:601-606, 1994; Rypacek et al., Pflugers Arch. 392:211-217, 1982; Yamoaka et al., J. Pharm. Pharmacol. 47:479-486, 1995, Francesco, Bioconjugate Chemistry 9(4):418-450, 1998, Duncan and Spreafico, Clin. Pharmacokinet. 27(4):290-306, 1994, which are hereby incorporated by reference.

Other features and advantages of the invention will be apparent from the following detailed description thereof, and from the claims.

DETAILED DESCRIPTION

Figure 1:
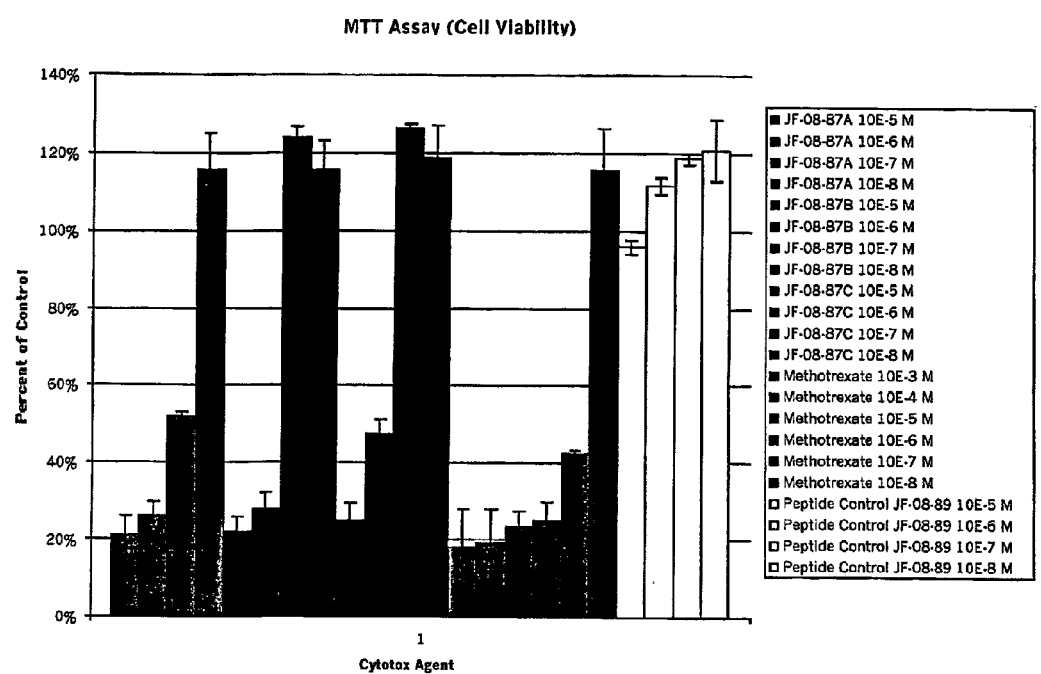
FIG. 1. is a graph showing the inhibitory effects of a typical methotrexate-somatostatin conjugate on proliferation of neuroblastoma IMR-32 cells compared to non-conjugated methotrexate and non-conjugated somatostatin analog segment. The equivalent potencies of methotrexate-peptide conjugate and methotrexate alone in this in vitro system are readily apparent. Control peptide JF-08-89 is D-Ser-D-Ser-D-Ser-D-Ser-D-Ser-Nle-D-Tyr-D-Ser-cyclo [Cys-Phe-D-Trp-Lys-Thr-Cys]-Thr-NH$_2$ (SEQ ID NO: 21).

A family of peptide agents has been developed that utilizes a novel, universal linking sequence. The linking sequence enables conjugation of therapeutic agents, cytotoxic agents, chelating groups, or detectable labels to biologically active peptides without substantial loss of biological potency of the targeting segment of the peptide agent. These peptide agents or analogs may additionally include a hydrophilic biodistribution enhancing segment in another aspect of the invention, increasing potency of treatment by targeting the analogs away from the liver towards rapid elimination via the kidney.

A peptide agent of the invention is of the general formula:

X-Y-Z-Q        (Formula I)

wherein X is optionally selected from cytotoxic agents, a therapeutic agents, detectable labels or chelating groups; Y is an hydrophilic element; Q is a biologically active peptide such as somatostatin or bombesin, and Z is a linking peptide that, when bonded to Q at the N-terminus or to a compatible side-chain amino group of Q, preserves at least 50% of the biological activity of Q. An example of a substitution of Q is position 6 of the GnRH peptides. This position is very tolerant of substitution of, for instance, D-Lys, the epsilon amino group of which could be used for the described attachment of cytotoxic or radioactive groups with retention of receptor affinity. Z has the formula: A-B-C-E-F (SEQ ID NO: 1) where A is D-Lys, D-Tyr, D-Ser, or L-Ser, or is deleted; B is D-Lys or D-Tyr, or deleted; C is Lys, Ser, hSer, Nle, Abu, Nva, (2,3, or 4) 3-pyridyl-Ala 9 (Pal), Orn, Dab, Dap, 4-NH$_2$-Phe, D-4-OH-Pro, or L-4-OH-Pro, or is deleted; E is D-Lys, D-Tyr, D-Ser, D-OH-Pro, L-4-OH-Pro, D-Asn, L-Asn, D-Asp, L-Asp, D-Glu, L-Glu, D-Gln, or L-Gln; and F is D-Lys, D-Tyr, D-Ser, D-OH-Pro, L-4-OH-Pro, 3-iodo-D-Tyr, 3-5 diido-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; provided that when A, B, C, and E are Tyr, Tyr, Lys, and Tyr, respecitively, F is not Lys; and when A, B, C, and E are Lys, Tyr, Lys, and Tyr, respectively, E is not Tyr or Lys; and when A and B are deleted, and C and E are Lys and Tyr, respectively, F is not Tyr or Lys. The Z peptide linker may thus be 2, 3, 4, or 5 residues in length.

Included among the peptide agents synthesized thus far are the following:

JF-07-100
MTXCOO-CH$_2$CO-D-Lys-D-Tyr-Lys-D-Tyr-D-Lys-Cys-Phe-D-Trp-Lys-Thr-Cys-Thr-NH$_2$        (SEQ ID NO: 24)

JF-08-87A
MTXCOO-CH$_2$CO-(D-Ser)$_5$-Lys-D-Tyr-D-Tyr-Cys-Phe-D-Trp-Lys-Thr-Cys-Thr-NH$_2$        (SEQ ID NO: 25)

JF-09-35
MTXCOONH-Leu-Ala-Leu-Ala-(D-Ser)$_5$-Lys-D-Tyr-D-Ser-Cys-Phe-D-Trp-Lys-Thr-Cys-Thr-NH$_2$        (SEQ ID NO: 26)

MTXCOO-CH$_2$CO-(D-Ser)$_5$-Lys-D-Tyr-D-Tyr-cyclo[Cys-Phe-D-Trp-Lys-Thr-Cys]-Thr-NH$_2$        (SEQ ID NO: 27)

MTXCOO-CH$_2$CO-(D-Ser-Ser)$_4$-Tyr-D-Ser-Gln-Trp-Ala-Val-β-Ala-His-Phe-Nle-NH$_2$        (SEQ ID NO: 28)

JF-09-73
Thiocolchicine-thioether-Lys-(D-Ser)$_{10}$-Nle-D-Tyr-D-Ser-cyclo[Cys-Phe-D-Trp-Lys-Thr-Cys]-Thr-NH$_2$        (SEQ ID NO: 29)

JF-09-93
Camptothecin-carbonyl-Sar-D-Ser-Nle-D-Tyr-D-Ser-cyclo[Cys-Phe-D-Trp-Lys-Thr-Cys]-Thr-NH$_2$        (SEQ ID NO: 30)

JF-09-95
Camptothecin-carbonyl-Pro-D-Ser-Nle-D-Tyr-D-Ser-cyclo[Cys-Phe-D-Trp-Lys-Thr-Cys]-Thr-NH$_2$        (SEQ ID NO: 31)

JF-09-99
Camptothecin-carbonyl-Hydroxyproline-D-Ser-Nle-D-Tyr-D-Ser-cyclo[Cys-Phe-D-Trp-Lys-Thr-Cys]-Thr-NH$_2$        (SEQ ID NO: 32)

Additional sequences of peptide agents of the invention are found in Table 1.

The present invention circumvents the accumulation of toxic peptide analog in tissues, through inclusion of both the Z linker, containing hydrophilic resides, and optional inclusion of an elongated hydrophilic linker. These linkers promote rapid elimination of intact, non-bound peptide agents through the kidneys. Polyethylene glycol (PEG), α, β-poly (N-hydroxyethyl)-DL-aspartamide (PHEA), and polyvinylalcohol (PVA) groups contained in this invention are also known to be excellent promoters of rapid renal secretion which is correlated generally with lower potential drug toxicities (Yamoaka et al., *J. Pharmacol. Sci.*, 83:601-606, 1994; Rypacek et al., *Pflugers Arch.*, 392:211-217, 1982; Yamoaka et al., *J. Pharm. Pharmacol.*, 47:479-486, 1995). We posit that these groups also promote lowered toxicity emanating from bioavailable, non-internalized conjugates.

The peptide agents of the invention include a universal linking sequence designed to preserve full biological potency of the peptide analogs when conjugated to a cytotoxic agent. A peptide analog of the invention has a biological potency that is preferably greater than or equal to the parent peptide analog from which it is derived, with a specificity that is greater, lesser, or equivalent to the parent peptide's target specificity. For example, a somatostatin analog may bind to more somatostatin receptor subtypes than naturally occurring somatostatin, or it may bind to a particular receptor subtype. Some analogs of the invention contain D-isomers of amino acids or analogs thereof, facilitating stable coupling of cytotoxic agents while retaining high receptor affinity and biological potency of the peptide analog. Preferably a cytotoxic agent will be coupled via a linkage likely to encourage release of free cytotoxic agent intracellularly.

Additionally, because the somatostatin analogs of the invention are variously hydrophilic, they are water-soluble and, thus, have enhanced use as compared to previous hydrophobic analogs. The hydrophilic analogs described herein are soluble in blood, cerebrospinal fluid, and other bodily fluids, as well as in urine, facilitating excretion by the kidneys. This hydrophilic character facilitates the delivery of the analogs of the invention to almost every area of the body. The invention also discloses specific hydrophilic elements for incorporation into peptide analogs, allowing modulation of the analog's hydrophilicity to adjust for the chemical and structural nature of the various conjugated cytotoxic agents.

Somatostatin agonist analogs are rapidly internalized after binding to their receptors (see Lukinius et al, *Acta Onc.*, 38:383-387, 1999) and can thus be used as vectors for targeting various therapeutic agents—such as traditional tumor cyctotoxic agents: It is possible that the specificity of such anti-tumor agents can be drastically improved since many tumor types heavily overexpress somatostatin type 2 receptors. In this manner, we propose that the toxic side effects associated with all conjugatable cytotoxic agents can be usefully lowered as long as a potent hybrid molecule can be designed which retains very high affinity for somatostatin receptors.

The invention features the use of a linking sequence, referred to as Z in formula I, which we have found enables many long N-terminal amino acid sequences and large molecules to be conjugated to the N-terminus of the somatostatin analogs with full retention of agonist potency. This linking sequence can be used to add longer, enzymatically stable (via use of D-amino acids), hydrophilic peptide sequences (the Y element of formula I) designed to target the resulting conjugates away from the liver towards rapid elimination via the kidney. Alternatively, a hydrophilic polymer may be linked to the peptide analog via the Z linker. This promotes lowered toxicity emanating from non-internalized conjugates.

The peptide analog also includes an element, denoted as Y in formula I, which may be optimized to facilitate biodistribution of the particular peptide agent conjugated to a cytoxic or therapeutic group, or a chelating group or detectable label. The Y linker may be a peptide or a polymer such as PEG or PVA. If Y is a hydrophilic peptide, Y may be 1 to 50 amino acids in length, or more preferably 3 to 15 residues in length. For example, Y may be 3, 4, 5, 6, 7, 8, 9, 10, 11, 12, 13, 14, 15, 16, 17, 18, 19 or 20 amino acid residues in length. When a peptide, Y may contain charged or non-polar amino acids, their analogs or derivatives that are naturally occurring, synthetic or modified.

The linking sequences of the invention are used to conjugate a biologically active peptide referred to as Q in formula I, to various therapeutic or diagnostic agents, referred to as X in formula I. The component X of formula I can be any known cytotoxic or therapeutic moiety, e.g., Antineoplastic agents such as: Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'-Bis(2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nitrosourea(fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis(platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); or 2-chlorodeoxyadenosine (2-Cda).

Other anti-neoplastic compounds include, but are not limited to, 20-pi-1,25 dihydroxyvitamin D3; 5-ethynyluracil; abiraterone; aclarubicin; acylfulvene; adecypenol; adozelesin; aldesleukin; all TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; rnerbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+ myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

X may also be an antiproliferative agent, for example piritrexim isothionate. Alternatively, X may be an antiprostatic hypertrophy agent such as, for example, sitogluside, a benign prostatic hyperplasia therapy agent such as, for example, tamsulosin hydrochloride, or a prostate growth inhibitor such as, for example, pentomone.

X can also be a radioactive agent, including, but not limited to: Fibrinogen $^{125}$I; Fludeoxyglucose $^{18}$F; Fluorodopa $^{18}$F; Insulin $^{125}$I; Insulin $^{131}$I; Iobenguane $^{123}$I; Iodipamide Sodium $^{131}$I; Iodoantipyrine $^{131}$I; Iodocholesterol $^{131}$I ; Iodohippurate Sodium $^{123}$I; Iodohippurate Sodium $^{125}$I; Iodohippurate Sodium $^{131}$I; Iodopyracet $^{125}$I; Iodopyracet $^{131}$I; Iofetamine Hydrochloride $^{123}$I; Iomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Tc Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I; Thyroxine $^{131}$I; Tolpovidone $^{131}$I; Triolein $^{251}$I; or Triolein $^{131}$I.

Therapeutic or cytotoxic agents may include, for example, anti-cancer Supplementary Potentiating Agents, including, but not limited to: Tricyclic anti-depressant drugs (e.g., imipramine, desipramine, amitryptyline, clomipramine, trimipramine, doxepin, nortriptyline, protriptyline, amoxapine, and maprotiline); non-tricyclic anti-depressant drugs (e.g., sertraline, trazodone, and citalopram); Ca++ antagonists (e.g., verapamil, nifedipine, nitrendipine, and caroverine); Calmodulin inhibitors (e.g., prenylamine, trifluoroperazine, and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

The compounds of the invention also can be administered with cytokines such as granulocyte colony stimulating factor. Preferred anticancer agents used in anti-cancer cocktails (e.g., in combination with the agents of the invention) include (some with their MTDs shown in parentheses): gemcitabine (1000 mg/m$^2$); methotrexate (15 gm/m$^2$ i.v.+ leuco.<500 mg/m$^2$ i.v. w/o leuco); 5-FU (500 mg/m$^2$/day×5 days); FUDR (100 mg/kg×5 in mice, 0.6 mg/kg/day in human i.a.); FdUMP; Hydroxyurea (35 mg/kg/d in man); Docetaxel (60-100 mg/m$^2$); discodermolide; epothilones; vincristine (1.4 mg/m$^2$); vinblastine (escalating: 3.3-11.1 mg/m$^2$, or rarely to 18.5 mg/m$^2$); vinorelbine (30 mg/m$^2$/wk); meta-pac; irinotecan (50-150 mg/m$^2$, 1×/wk depending on patient response); SN-38 (~100 times more potent than Irinotecan); 10-OH campto; topotecan (1.5 mg/m$^2$/day in humans, 1×iv LD10 mice=75 mg/m$^2$); etoposide (100 mg/m$^2$ in man); adriamycin; flavopiridol; Cis-Pt (100 mg/m$^2$ in man); carbo-Pt (360 mg/m$^2$ in man); bleomycin (20 mg/m2); mitomycin C (20 mg/m$^2$); mithramycin (30 sug/kg); capecitabine (2.5 g/m$^2$ orally); cytarabine (100 mg/m$^2$/day); 2-Cl-2'deoxyadenosine; Fludarabine-P04 (25 mg/m$^2$/day, ×5 days); mitoxantrone (12-14 mg/m$^2$); mitozolomide (>400 mg/m$^2$); Pentostatin; or Tomudex.

X may preferably be an antimetabolic agent, such as methotrexate. Antimetabolites include, but are not limited to, the following compounds and their derivatives: azathioprine, cladribine, cytarabine, dacarbazine, fludarabine phosphate, fluorouracil, gencitabine chlorhydrate, mercaptopurine, methotrexate, mitobronitol, mitotane, proguanil chlorhydrate, pyrimethamine, raltitrexed, trimetrexate glucuronate, urethane, vinblastine sulfate, vincristine sulfate, etc. More preferably, X may be a folic acid-type antimetabolite, a class of agents that includes, for example, methotrexate, proguanil chlorhydrate, pyrimethanime, trimethoprime, or trimetrexate glucuronate, or derivatives of these compounds.

In another embodiment, X may be a member of the anthracycline family of neoplastic agents, including but not limited to aclarubicine chlorhydrate, daunorubicine chlorhydrate, doxorubicine chlorhydrate, epirubicine chlorhydrate, idarubicine chlorhydrate, pirarubicine, or zorubicine chlorhydrate. Furthermore, X may be a camptothecin, or its derivatives or related compounds such as 10, 11 methylenedioxycamptothecin. X may also be selected from the maytansinoid family of compounds, which includes a variety of structurally related compounds. For example, ansamitocin P3, maytansine, 2'-N-demethylmaytanbutine, or maytanbicyclinol are maytansinoids.

The peptide agents of the invention can be modified or labeled to facilitate diagnostic or therapeutic uses. Detectable labels such as a radioactive, fluorescent, heavy metal, or other agents may be bound to the peptide agents of the invention. Single, dual, or multiple labeling of a peptide agent may be advantageous. For example, dual labeling with radioactive iodination of one or more residues combined with the additional coupling of, for example, $^{90}$Y via a chelating group to amine-containing side or reactive groups, would allow combination labeling. This may be useful for specialized diagnostic needs such as identification of widely dispersed small neoplastic cell masses.

Peptide analogs of the invention may also be modified, for example, by halogenation of the tyrosine residues of the compound. Halogens include fluorine, chlorine, bromine, iodine, or astatine. Such halogenated peptide agents may be detectably labeled, e.g. if the halogen is a radioisotope such as, for example, $^{18}$F, $^{75}$Br, $^{77}$Br, $^{122}$I, $^{123}$I, $^{124}$I, $^{125}$I, $^{129}$I, $^{131}$I, or $^{211}$At. Halogenated compounds of the invention contain a halogen covalently bound to at least one amino acid, and preferably to D-Tyr residues in each peptide agent molecule. Other suitable detectable modifications include binding of other compounds (e.g., a fluorochrome such as fluorescein) to a lysine residue of the analog, particularly an analog having a linker including lysines.

Radioisotopes for radiolabeling the biological peptide agents of the invention include any radioisotope that can be covalently bound to a residue of the analog. The radioisotopes can be selected from radioisotopes that emit either beta or gamma radiation, or alternatively, the peptide agents can be modified to contain chelating groups that, for example, can be covalently bonded to lysine residue(s) of the analog. The chelating groups can then be modified to contain any of a variety of radioisotopes, such as gallium, indium, technetium, ytterbium, rhenium, or thallium (e.g., $^{125}$I, $^{67}$Ga, $^{111}$In, $^{99m}$Tc, $^{169}$Yb, $^{186}$Re).

Where the peptide agent is modified by attachment of a radioisotope, preferable radioisotopes are those having a radioactive half-life corresponding to, or longer than, the biological half-life of the agent used. More preferably, the radioisotope is a radioisotope of a halogen atom (e.g. a radioisotope of fluorine, chlorine, bromine, iodine, and astatine), even more preferably $^{75}$Br, $^{77}$Br, $^{76}$Br, $^{122}$I, $^{123}$I, $^{124}$I, $^{125}$I, $^{129}$I, $^{131}$I, or $^{211}$At.

Conjugates that include radioactive metals are useful in radiographic imaging or radiotherapy. Preferred radioisotopes also include $^{99m}$Tc, $^{51}$Cr, $^{67}$Ga, $^{68}$Ga, $^{111}$In, $^{168}$Yb, $^{140}$La, $^{90}$Y, $^{88}$Y, $^{153}$Sm, $^{156}$Ho, $^{165}$Dy, $^{64}$Cu, $^{97}$Ru, $^{103}$Ru, $^{186}$Re, $^{188}$Re, $^{203}$Pb, $^{211}$Bi, $^{212}$Bi, $^{213}$Bi, and $^{214}$Bi. The choice of metal is determined based on the desired therapeutic or diagnostic application.

The metal complexes of the invention are useful as diagnostic and/or therapeutic agents. A detectable label may be a metal ion from heavy elements or rare earth ions, such as $Gd^{3+}$, $Fe^{3+}$, $Mn^{3+}$, or $Cr^{2+}$. Conjugates that include paramagnetic or superparamagnetic metals are useful as diagnostic agents in MRI imaging applications. Paramagnetic metals that may be used in the conjugates include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Preferably, the polymer has a relaxtivity of at least 10, 12, 15, or 20 mM$^{-1}$ sec$^{-1}$ Z$^{-1}$, wherein Z is the concentration of paramagnetic metal.

Chelating groups may be used to indirectly couple detectable labels or other molecules to the peptide agents of the invention. Chelating groups may link peptide agents with radiolabels, such as a bifunctional stable chelator may be linked to one or more terminal or internal amino acid reactive groups. They may be linked via an isothiocyanate β-Ala or appropriate non α-amino acid linker which prevents Edman degradation. Examples of chelators known in the art include, for example, the ininocarboxylic and polyaminopolycarboxylic reactive groups, DTPA (N,N-Bis [2-[bis(carboxymethyl)amino]ethyl]glycine), and DOTA (1,4,7,10-tetraaazacyclododecane-1,4,7,10-tetraacetic acid).

The cytotoxic or therapeutic conjugates of the invention can employ any of the large number of known somatostatin analogs that recognize the somatostatin receptor, e.g., those described in the definitions above. Preferably, the somatostatin analog portion of the conjugate contains between 10 and 18 amino acids, and includes the core sequence: cyclo[Cys-Phe-D-Trp-Lys-Thr-Cys] (SEQ ID NO: 33). Preferably, the C-terminus of the analog is: Thr-NH$_2$ (SEQ ID NO: 34). Bombesin analogs as disclosed herein may also be conjugated to cytotoxic or therapeutic agents in the peptide agents of the invention.

The somatostatin analog can be coupled directly to the cytotoxic or therapeutic agent using known chemical methods, or the two moieties can be coupled via an indirect linkage. For example, the analog may be attached to a chelating group that is attached to the cytotoxic or therapeutic agent. Chelating groups include, but are not limited to, an iminodicarboxylic group or a polyaminopolycarboxylic group. For general methods, see, e.g., Liu et al., *Bioconjugate Chem.* 12(4):653, 2001; Cheng et al., WO 89/12631; Kieffer et al., WO 93/12112; Albert et al., U.S. Pat. No. 5,753,627; and WO 91/01144 (each of which are hereby incorporated by reference).

Specific targeting of labeled, therapeutic or cytotoxic agents allows selective destruction of tumors expressing receptors specific for biologically active peptides. For example, the tumors expressing somatostatin receptors includes neoplasms of the lung, breast, prostate, colon, brain, gastrointestinal tract, neuroendocrine axis, liver, kidney, etc. (see Schaer et al., *Int. J. Cancer,* 70:530-537, 1997; Chave et al., *Br. J. Cancer* 82(1):124-130, 2000; Evans et al., *Br. J. Cancer* 75(6):798-803, 1997). Cytotoxic somatostatin peptide analogs may also be specific for tumor vasculatures, or angiogenic blood vessels, such as those which overexpress somatostatin receptors (see Denzler and Reubi, *Cancer* 85:188-198, 1999; Gulec et al., *J. Surg. Res.* 97(2): 131-137, 2001; Woltering et al., *J. Surg. Res.* 50:245, 1991).

Peptide agents of the invention may be administered to a mammalian subject, such as a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, (18th edition), ed. A. Gennaro, 1990, Mack Publishing Company, Easton, Pa.

Pharmaceutical formulations of a therapeutically effective amount of a peptide agent of the invention, or pharmaceutically acceptable salt-thereof, can be administered orally, parenterally (e.g., intramuscular, intraperitoneal, intravenous, or subcutaneous injection, inhalation, intradermally, optical drops, or implant), nasally, vaginally, rectally, sublingually, or topically, in admixture with a pharmaceutically acceptable carrier adapted for the route of administration.

Methods well known in the art for making formulations are found, for example, in *Remington's Pharmaceutical Sciences* (18th edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the polypeptides of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

Compositions for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the polypeptide being administered, the time of administration, the route of administration, the nature of the formulation, the rate of excretion, the nature of the subject's conditions, and the age, weight, health, and gender of the patient. In addition, the severity of the condition targeted by the biologically active peptide such as somatostatin or bombesin will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The polypeptides of the invention can be administered in a sustained release composition, such as those described in, for example, U.S. Pat. Nos. 5,672,659 and 5,595,760. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

Polypeptides of the present invention can be prepared in any suitable manner. The polypeptides may be isolated from naturally occurring sources, recombinantly produced, or produced synthetically, or produced by a combination of these methods. The synthesis of short peptides is well known in the art. See e.g., Stewart et al., Solid Phase Peptide Synthesis (Pierce Chemical Co., 2d ed., 1984). The peptides of the present invention can be synthesized according to standard peptide synthesis methods known in the art and exemplified in Example 1 below.

The present invention is illustrated by the following examples, which are in no way intended to be limiting of the invention.

EXAMPLE 1

Preparation of di-cesium Salt of (+)-amethopterin (methotrexate)

Methotrexate (0.75 mmole) was dissolved in 200 ml of water to which was added cesium bicarbonate (1.5 mmol). The yellow solution was stirred for 4 hours, evaporated under reduced pressure, and the oily residue dissolved in ethanol. This was evaporated from anhydrous ethanol 3 times to remove residual water.

EXAMPLE 2

Preparation of 2-bromo-acetyl-D-tert-butyl-Ser-D-tert-butyl-Ser-D-tert-butyl-Ser-D -tert-butyl-Ser-D-tert-butyl-Ser-epsilon-tert-butyloxycarbonyl-Lys-D-tert-butyl-Tyr -D-tert-butyl-Tyr-S-trityl-Cys-Phe-D-Trp-epsilon-tert-butyloxycarbonyl-Lys-tert-butyl-Thr-S-trityl-Cys-tert-butyl-Thr-Rink-amide-resin (SEQ ID NO: 24)

Rink amide MBHA polystyrene resin (0.25 mmole) [4-(2',4'-dimethoxyphenyl-Fmoc-(aminomethyl)phenoxyacetamido-norleucyl-methylbenzhydrylamine resin, 100-200 mesh, Novabiochem, San Diego, Calif.] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Thr(tBut) (0.75 mmol), diisopropylcarbodiimide (DIC) (0.75 mmol), and N-hydroxybenzotriazole monohydrate (HOBt) (0.75 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-t-butyl-L-threonine, $N^\alpha$-Fmoc-$N^\epsilon$-Boc-L-lysine, $N^\alpha$-Fmoc-$N^{in}$-Boc-D-tryptophan, Fmoc-L-phenylalanine, Fmoc-S-trityl-L-cysteine, Fmoc-O-t-butyl-D-tyrosine, Fmoc-O-t-butyl-D-tyrosine, $N^\alpha$-Fmoc-$N^\epsilon$-Boc-L-lysine, Fmoc-O-t-butyl-D-serine, Fmoc-O-t-butyl-D-serine, Fmoc-O-t-butyl-D-serine, Fmoc-O-t-butyl-D-serine, Fmoc-O-t-butyl-D-serine. After removal of the final Fmoc group, 2-bromoacetic acid was coupled to the N-terminal amino group using the same coupling reagents.

EXAMPLE 3

Preparation of methotrexate-acetyl-D-tert-butyl-Ser-D-tert-butyl-Ser-D-tert-butyl-Ser -D-tert-butyl-Ser-D-tert-butyl-Ser-epsilon-tert-butyloxycarbonyl-Lys-D-tert-butyl -Tyr-D-tert-butyl-Tyr-S-trityl-Cys-Phe-D-Trp-epsilon-tert-butyloxycarbonyl-Lys-tert-butyl-Thr-S-trityl-Cys-tert-butyl-Thr-Rink-amide-resin (SEQ ID NO: 24)

The di-cesium salt of methotrexate (0.75 mmol) prepared in Example 1 was dissolved in DMSO and added to peptidyl resin (0.25 mmol) prepared in Example 2 in a round bottom flask. The suspension was gently mixed while heating in a water bath (40° C., 18 h), filtered, and washed with copious amounts of DMF followed by methanol. After a final filtration the derivatized resin was air dried overnight.

EXAMPLE 4

Preparation of methotrexate-acetyl-D-Ser-D-Ser-D-Ser-D-Ser-D-Ser-Lys-D-Tyr-D-Tyr-cyclo[Cys-Phe-D-Trp-Lys-Thr-Cys]-Thr-amide (SEQ ID NO: 26)

The methotrexate-peptide resin prepared in Example 3 (0.25 mmol) was placed in a round bottomed flask to which was added 15 ml of a solution of trifluoroacetic acid (TFA) containing water (2.5%), 1,2-ethanedithiol (2.5%), and triisopropylsilane (1%). The suspension was agitated (2 h), filtered, and washed several times with TFA. The TFA was evaporated in vacuo and ether added to the resulting oil to give a yellow powder which was then dissolved in 60% acetic acid (250 ml). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 ml in vacuo and the crude methotrexate peptide purified by preparative reverse phase high pressure liquid chromatography (RP-hplc) on a column (21.4×250 mm) of C-18 bonded silica (Dynamax 300, 8 μm). A linear gradient elution system at a flow rate of 20 mL/min was employed: buffer A consisted of 0.1% TFA and buffer B, 0.1% TFA in 80% MeCN; 20% B to 50% B was increased at 1% per min. The separation were monitored at 280 nm. The fractions containing the pure product as evidenced by analytical hplc were pooled, concentrated in vacuo, and subjected to lyophilization. The peptide was obtained as a fluffy white powder of constant weight by lyophilization from aqueous acetic acid. Correct composition was demonstrated by amino acid analysis of an acid hydrolysate and matrix assisted laser desorption mass spectrometry.

EXAMPLE 5

Preparation of 2-bromo-acetyl-D-tert-butyl-Ser-tert-butyl-Ser-D-tert-butyl-Ser-tert -butyl-Ser-D-tert-butyl-Ser-tert-butyl-Ser-D-tert-butyl-Ser-tert-butyl-Ser-D-tert-butyl-Ser-tert-butyl-Ser-D-tert -butyl-Tyr-D-tert-butyl-Ser-Gln-Trp-Ala-Val-β-Ala-tert-butyloxycarbonyl-His-Phe-Nle-Rink-amide-resin (SEQ ID NO: 27)

Rink amide MBHA polystyrene resin (0.25 mmole) [4-2', 4'-dimethoxyphenyl-Fmoc-(aminomethyl)phenoxyacetamido-norleucyl-methylbenzhydrylamine resin, 100-200 mesh, (Novabiochem, San Diego, Calif.] was added to the reaction vessel of a CS136 automatic peptide synthesizer (CS Bio, Inc., San Carlos, Calif.), and swollen in DMF for approximately 1 hour. The resin was filtered and an excess of 20% piperdine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Nle (0.75 mmol), diisopropylcarbodiimide (DIC) (0.75 mmol), and N-hydroxybenzotriazole monohydrate (HOBt) (0.75 mmol) were all dissolved in DMF and added to the resin which was mixed (1 h) followed by washing 4 times with DMF.

The Fmoc group was again removed by treatment with 20% piperidine/DMF solution and the remaining amino acid derivatives and 2 bromoacetic acid were coupled as described in Example 2 using the same coupling reagents.

EXAMPLE 6

Preparation of methotrexate-acetyl-D-tert-butyl-Ser-tert-butyl-Ser-D-tert-butyl-Ser -tert-butyl-Ser-D-tert-butyl-Ser-tert-butyl-Ser-D-tert-butyl-Ser-tert-butyl-Ser-D -tert-butyl-Tyr-D-tert-butyl-Ser-Gln-Trp-Ala-Val-β-Ala-tert-butyloxycarbonyl-His-Phe-Nle-Rink-amide-resin (SEQ ID NO: 27)

The di-cesium salt of methotrexate (0.75 mmol) prepared in Example 1 was dissolved in DMSO and added to peptidyl resin (0.25 mmol) prepared in Example 5 in a round bottom flask. The suspension was gently mixed while heating in a water bath (40° C., 18 h), filtered, and washed with copious amounts of DMF followed by methanol. After a final filtration the derivatized resin was air dried overnight.

EXAMPLE 7

Methotrexate-acetyl-D-Ser-Ser-D-     (SEQ ID NO: 27)

Ser-Ser-D-Ser-Ser-D-Ser-Ser-Tyr-

D-Ser-Gln-Trp-Ala-Val-β-Ala-His-

Phe-Nle-NH$_2$.

The methotrexate-peptide resin prepared in Example 6 (0.25 mmol) was placed in a round bottomed flask to which was added 15 ml of a solution of trifluoroacetic acid (TFA) containing water (2.5%), 1,2 ethanedithiol (2.5%), and tri-isopropylsilane (1%). The suspension was agitated (2 h), filtered, and washed several times with TFA. The TFA was evaporated in vacuo and ether was added to the resulting oil to give a yellow powder.

The methotrexate peptide was purified by preparative reverse phase high pressure liquid chromatography (RP-hplc) on a column (21.4×250 mm) of C-18 bonded silica (Dynamax 300 m 8 μm). A linear gradient elution system at a flow rate of 20 mL/min was employed: buffer A consisted of 0.1% TFA and buffer B, 0.1% TFA in 80% MeCN; 20% B to 50% B was increased at 1%/min. The separation was monitored at 280 nm. The fractions containing the pure product as evidenced by analytical HPLC were pooled, concentrated in vacuo, and subjected to lyophilization. The peptide was obtained as a fluffy white powder of constant weight by lyophylization from aqueous acetic acid. Correct composition was demonstrated by amino acid analysis of an acid hydrolysate and matrix assisted laser desorption mass spectrometry.

EXAMPLE 8

Effects of Cytotoxic Agent-peptide Conjugates on Tumor Cell Proliferation

A CellTiter 96 cell proliferation kit was used according to the described protocols (Promega Corporation, Madison, Wis.)). Culture medium (50 μl) containing various concentrations of different peptides was added respectively in each well of the 96-well kit plates followed by 50 μl of a suspension containing 5,000 cultured IMR-32 tumor cells. The plate was incubated at 37° C. for different times up to and including 7 days in a humidified, 5% $CO_2$ atmosphere. Kit dye solution (15 μl ) was added to each well and the plate incubated the plates at 37° C. for 4 hours in a humidified, 5% $CO_2$ atmosphere. After 4 hours, 100 μl of the solubilization/stop solution were added to each well and incubation was continued at 37° C. for 1 hour or more until complete solubilization of the formazan crystals occurred. Absorbencies of individual well solutions were then measured at 570 nm wavelength using a 96 well plate reader.

EXAMPLE 9

In vitro Effects of Somatostatin Analogs on Rat Pituitary GH Release

This is a primary system for evaluating SRIF analog potency and can be considered a somatostatin subtype 2 rat receptor related system which historically also correlates well with human subtype 2 binding.

Anterior pituitaries from adult male rats weighing 200-250 g and housed under controlled conditions (lights on from 0500-1900 h), are dispersed using aseptic techniques by a trypsin/DNase method. The dispersed cells are diluted with sterile-filtered Dulbecco's modified Eagle medium (MEM) (Gibco Laboratories, Grand Island, N.Y. (GIBCO)), which is supplemented with 2.5% fetal calf serum (GIBCO), 3% horse serum (GIBCO), 10% fresh rat serum (stored on ice for no longer than 1 h) from the pituitary donors, 1% MEM nonessential amino acids (GIBCO), gentamycin (10 ng/ml; Sigma), and nystatin (10,000 U/ml; GIBCO). The cells are counted with a hemacytometer (approximately 2,000,000 cells per pituitary) and randomly plated at a density of 200,000 cells per well (Co-star cluster 24; Rochester Scientific Co., Rochester, N.Y.). The plated cells are maintained in the above Dulbecco's medium in a humidified atmosphere of 95% air and 5% $CO_2$ at 37° C. for 96 h.

In preparation for a hormone challenge, the cells are washed 3× with medium 199 (GIBCO) to remove old medium and floating cells. Each dose of secretagogue (diluted in siliconized test tubes) was tested in quadruplicate wells in a total volume of 1 ml medium 199 containing 1% BSA (fraction V; Sigma Chemical Co., St. Louis, Mo.). Cells are pulsed with SS or SS analogs doses in the presence of GH-stimulatory 1 nM GRH(1-29)NH$_2$. After 3 h at 37° C. in an air/carbon dioxide atmosphere (95/5%), the medium is removed and stored at 20° C. until assayed for hormone content. GH in plasma and media is measured by a standard double antibody RIA using components supplied by the NIDDK and the National Hormone and Pituitary Program.

EXAMPLE 10

Preparation of O-benzyl-D-Ser-O-benzyl-D-Ser-O-benzyl-D-Ser O-benzyl-D-Ser-O-benzyl-D-Ser-L-Nle-O-2,6-dichlorobenzyl-D-Tyr-O-benzyl-D-Ser-S-4-methylbenzyl-L-Cys-L-Phe-D-Trp-N$^\epsilon$-(2-chlorobenzyloxycarbonyl)-L-Lys-O-benzyl-L-Thr-S-4-methylbenzyl-L-Cys-O-benzyl-L-Thr-MBHA Resin (SEQ ID NO: 35)

Methylbenzhydrylamine (MBHA) polystyrene resin (Bachem, Inc., Torrance. Calif.) (0.25 mmole) was added to the reaction vessel of a CS136 automatic peptide synthesizer (CS Bio, Inc., San Carlos, Calif.) and swollen in methylene chloride (DCM) for approximately 1 hour. The resin was filtered and an excess of 10% diisopropylethylamine (DI-PEA) was added and mixed for two minutes. The resin was filtered and again an excess amount of 10% DIPEA added and mixed for 5 minutes to ensure complete neutralization of the resin. After neutralization, the resin was washed 4 times with DCM and then the first protected amino acid, Boc-Thr (Bzl)-OH (0.75 mmol), diisopropylcarbodiimide (DIC) (0.75 mmol), and N-hydroxybenzotriazole monohydrate (HOBt) (0.75 mmol) were all dissolved in DMF and added to the resin which was mixed (1 h) followed by washing 4 times with DCM.

The tBoc group was removed by adding an excess of 40% Trifluoroacetic Acid (TFA) DCM and mixed for 2 minutes. The resin was filtered and again an excess amount of 40% TFA added and mixed for 20 minutes to ensure complete removal of the N-terminal tBoc. The resin was filtered and an excess of 10% diisopropylethylamine (DIPEA) was added and mixed for two minutes. The resin was filtered and again an excess amount of 10% DIPEA added and mixed for 5 minutes to ensure complete neutralization of the resin.

After neutralization, the resin was washed 4 times with DCM and then following the same general coupling procedures, the following amino acids were successively reacted with the growing peptide chain: Boc-S-4-methylbenzyl-L-cysteine, Boc-O-benzyl-L-threonine, N$^\alpha$-Boc-N$^\epsilon$-(2-chlorobenzyloxycarbonyl)-L-lysine, Boc-D-tryptophan, Boc-L-phenylalanine, Boc-S-4-methylbenzyl-L-cysteine, Boc-O-benzyl-D-serine, Boc-O-2,6-dichlorobenzyl-D-tyrosine, Boc-norleucine, Boc-O-benzyl-D-serine, Boc-O-benzyl-D-serine, Boc-O-benzyl-D-serine, Boc-O-benzyl-D-serine, Boc-O-benzyl-D-serine. The resin was finally washed 4 times with methanol and left overnight to dry.

EXAMPLE 11

Preparation of D-Ser-D-Ser-D-Ser-D-Ser-D-Ser-L-Norleucine-D-Tyr-D-Ser-cyclo[L-Cys-L-Phe-D-Trp-L-Lys-L-Thr-L-Cys]-L-Thr-NH$_2$ (SEQ ID NO: 36)

The peptidyl resin from Example 10 along with 5 mL of anisole was placed in a Teflon apparatus appropriate for anhydrous hydrogen fluoride manipulation. The reaction vessel was cooled in an alcohol/dry ice bath for 5 minutes and then 35 mL of gaseous anhydrous fluoride (HF) was condensed into the reaction vessel. The bath was changed from dry ice to regular ice and allowed to mix for one hour, then the HF was purged from the reaction vessel with a stream of nitrogen. The peptide was precipitated 3 times with excess ethyl ether and filtered. The filtered, crude peptide was dissolved in 60-90 percent acetic acid (250 ml). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 ml in vacuo and the crude peptide purified by preparative reverse phase high pressure liquid chromatography (RP-hplc) on a column (21.4×250 mm) of C-18 bonded silica (Dynamax 300, 8 μm). A linear gradient elution system at a flow rate of 20 mL/min was employed: buffer A consisted of 0.1% TFA and buffer B, 0.1% TFA in 80% MeCN; 20% B to 50% B was increased at 1% per minute. The separations were monitored at 280 nm. The fractions containing the pure product as evidenced by analytical HPLC were pooled, concentrated in vacuo and subjected to lyophilization. The peptide was obtained as a fluffy white powder of constant weight by lyophilization from aqueous acetic acid. Correct composition was demonstrated by amino acid analysis of an acid hydrolysate and matrix assisted laser desorption mass spectrometry.

EXAMPLE 12

Preparation of D-Ser-D-Ser-D-Ser-D-Ser-D-Ser-L-Lys-3-$^{125}$I-D-Tyr-D-Ser-cyclo[L-Cys-L-Phe-D-Trp-L-Lys-L-Thr-L-Cys]-L-Thr-NH$_2$ (SEQ ID NO: 22)

A modified Chloramine-T reaction was used to iodinate the peptide prepared in Example 11. Phosphate buffer (200 μL of 0.05M) was added to a septum-sealed vial containing 20 mCi of $^{125}$iodine and this served as the reaction vessel. Once neutralized, 9.411×10$^{-8}$ moles of peptide dissolved in 100 μL phosphate buffer were injected into the reaction vial. To start the iodination reaction, 4.29×10$^{-7}$ moles of chloramine-T were injected into the reaction vial in 50 μL of buffer. The reaction vessel was vortexed rapidly for 15-20 seconds and then the reaction halted by injecting 4.3×10$^{-6}$ moles of sodium metabisulfite in 50 μL.

Purification:

A C18 SepPak Lite cartridge (Waters Corp., Milford, Mass.) was used to purify the peptide from reactants. The SepPak was activated by washing with 10 mL of absolute ethanol at a flow rate of 1 mL/min. The SepPak was then washed with 10 mL of H$_2$O. The radioactive reaction mixture was then applied to the SepPak followed by 3×3-mL washes of the reaction vessel with 5% ethanol. The peptide was separated from the rest of the reactants by washing the SepPak with 10 mL of 20% ethanol. The peptide was finally eluted off the column in 250 μL aliquots using a solution of 80% ethanol in 0.01 N HCL and collected into 2 mL sterile screw cap vials.

EXAMPLE 13

Preparation of O-benzyl-D-Ser-O-benzyl-D-Ser-O-benzyl-D-Ser-O-benzyl-D-Ser-O -benzyl-D-Ser-O-benzyl-D-Ser-O-benzyl-D-Ser-O-benzyl-D-Ser-O-benzyl-D-Ser-O-benzyl-D-Ser-N$^\epsilon$-(2-chlorobenzyloxycarbonyl)-L-Lys-O-2,6-dichlorobenzyl-L-Tyr-O-2,6-dichlorobenzyl-L-Tyr-S-4-methylbenzyl-L-Cys-L-Phe-D-Trp-N$^\epsilon$-(2-chlorobenzyloxycarbonyl)-L-Lys-O-benzyl-L-Thr-S-4-methylbenzyl-L-Cys-O-benzyl-L-Thr-MBHA Resin (SEQ ID NO: 37)

Methylbenzhydrylamine (MBHA) polystyrene resin (Bachem, Inc., Torrance. Calif.) (0.25 mmole) was added to the reaction vessel of a CS136 automatic peptide synthesizer (CS Bio, Inc., San Carlos, Calif.) and swollen in methylene chloride (DCM) for approximately 1 hour. The resin was filtered and an excess of 10% diisopropylethylamine (DIPEA) was added and mixed for two minutes. The resin was filtered and again an excess amount of 10% DIPEA added and mixed for 5 minutes to ensure complete neutralization of the resin. After neutralization, the resin was washed 4 times with DCM and then the first protected amino acid, Boc-Thr (Bzl)-OH (0.75 mmol), diisopropylcarbodiimide (DIC) (0.75 mmol), and N-hydroxybenzotriazole monohydrate (HOBt) (0.75 mmol) were all dissolved in DMF and added to the resin which was mixed (1 h) followed by washing 4 times with DCM.

The tBoc group was removed by adding an excess of 40% trifluoroacetic acid (TFA) DCM and mixed for 2 minutes. The resin was filtered and again an excess amount of 40% TFA added and mixed for 20 minutes to ensure complete removal of the N-terminal tBoc. The resin was filtered and an excess of 10% diisopropylethylamine (DIPEA) was added and mixed for two minutes. The resin was filtered and again an excess amount of 10% DIPEA added and mixed for 5 minutes to ensure complete neutralization of the resin. After neutralization, the resin was washed 4 times with DCM and then following the same general coupling procedures, the following amino acids were successively reacted with the growing peptide chain Boc-S-4-methylbenzyl-L-cysteine, Boc-O-benzyl-L-threonine, N$^\alpha$-Boc-N$^\epsilon$-(2-chlorobenzyloxycarbonyl)-L-lysine, Boc-D-tryptophan, Boc-L-phenylalanine, Boc-S-4-methylbenzyl-L-cysteine, Boc-O-2,6-dichlorobenzyl-D-tyrosine, Boc-O-2,6-dichlorobenzyl-D-tyrosine, N$^\alpha$-Boc-N$^\epsilon$-(2-chlorobenzyloxycarbonyl)-L-lysine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine. The final Boc group was removed, the peptide neutralized, and washed using the same general procedure as above.

EXAMPLE 14

Preparation of DOTA-O-benzyl-D-Ser-O-benzyl-D-Ser-O-benzyl-D-Ser-O-benzyl -D-Ser-O-benzyl-D-Ser-O-benzyl-D-Ser-O-benzyl-D-Ser-O-benzyl-D-Ser-O-benzyl-D-Ser-O-benzyl-D-Ser-N$^\epsilon$-(2-chlorobenzyloxycarbonyl)-L-Lys-O-2,6-dichlorobenzyl-L-Tyr-O-2,6-dichlorobenzyl-L-Tyr-S-4-methylbenzyl-L-Cys-L-Phe-D-Trp-N$^\epsilon$-(2-chlorobenzyloxycarbonyl)-L-Lys-O-benzyl-L-Thr-S-4-methylbenzyl-L-Cys-O-benzyl-L-Thr-MBHA Resin (SEQ ID NO: 37)

In order to couple DOTA, which is very insoluble in organic solvents including DMF and DMSO alone, to the free amino group of the growing chain, a novel procedure utilizing the unexpected solubilizing effects of HOBt was used. First, 5 mmol of HOBT was dissolved in a beaker containing 50-75 mL of DMSO, then 1.25 mmol of DOTA were added and the suspension vigorously mixed until the DOTA went into solution. DIC (1.25 mmol) was added to the beaker and this mixture was added to the peptidyl resin, mixed overnight, and then washed 4 times with DMF and 4 times with methanol.

EXAMPLE 15

Preparation of DOTA-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-NH$_2$ (SEQ ID NO: 38)

The protected peptide resin described in Example 14 was subjected to cleavage from the resin and removal of side-chain protecting groups using liquid HF as described in Example 12. The free peptide was then cyclized and purified also as described in Example 12.

EXAMPLE 16

Preparation of D-O-benzyl-Ser-O-benzyl-Ser-D-O-benzyl-Ser-O-benzyl-Ser-D-O-benzyl -Ser-O-benzyl-Ser-D-O-benzyl-Ser-O-benzyl-Ser-D-O-dichlorobenzyl-Tyr-D-O-benzyl-Ser-Gln-Trp-Ala-Val-β-Ala-tosyl-His-Phe-Nle-MBHA Resin (SEQ ID NO: 27)

Methylbenzhydrylamine (MBHA) polystyrene resin (Bachem, Inc., Torrance. Calif.) (0.25 mmole) was added to the reaction vessel of a CS136 automatic peptide synthesizer (CS Bio, Inc., San Carlos, Calif.) and the peptide was assembled by successive additions of amino acid derivatives as described in Example 13.

EXAMPLE 17

D-Ser-Ser-D-Ser-Ser-D-Ser-Ser-D-Ser-Ser-D-Tyr-D-Ser-Gln-Trp-Ala-Val-β-Ala-His-Phe-Nle-NH$_2$. (SEQ ID NO: 27)

The protected peptide resin described in Example 16 was subjected to cleavage from the resin and removal of side-chain protecting groups using liquid HF as described in Example 12. The free peptide was then purified also as described in Example 12.

EXAMPLE 18

In vitro Effects of Bombesin Agonist Analogs on Guinea Pig Pancreatic Acinar Cell Amylase Release Dispersed acini from one guinea pig pancreas were suspended in 150 ml of standard incubation solution and samples (250 ml) were incubated for 30 min at 37° C., and amylase release was determined by the Phadebas reagent method. Amylase release was calculated as the percentage of amylase activity in the acini at the beginning of the incubation that was released into the extracellular medium during the incubation. Various concentrations of bombesin standard and analogs were incubated at various concentrations in order to determine half-maximal stimulation values ($EC_{50}$).

EXAMPLE 19

Biodistribution of $^{125}$I labeled JF-08-73 (Succinate-D-Asp-D-Ser-D-Ser-D-Ser-D-Ser-D-Ser-D-Asp-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-NH$_2$ (SEQ ID NO: 21) and JF-08-53 (D-Ser-D-Ser-D-Ser-D-Ser-D-Ser-L-Lys-D-Tyr-D-Ser-cyclo [L-Cys-L-Phe-D-Trp-L-Lys-L-Thr-L-Cys]-L-Thr-NH$_2$ (SEQ ID NO: 22)

Figure 2:
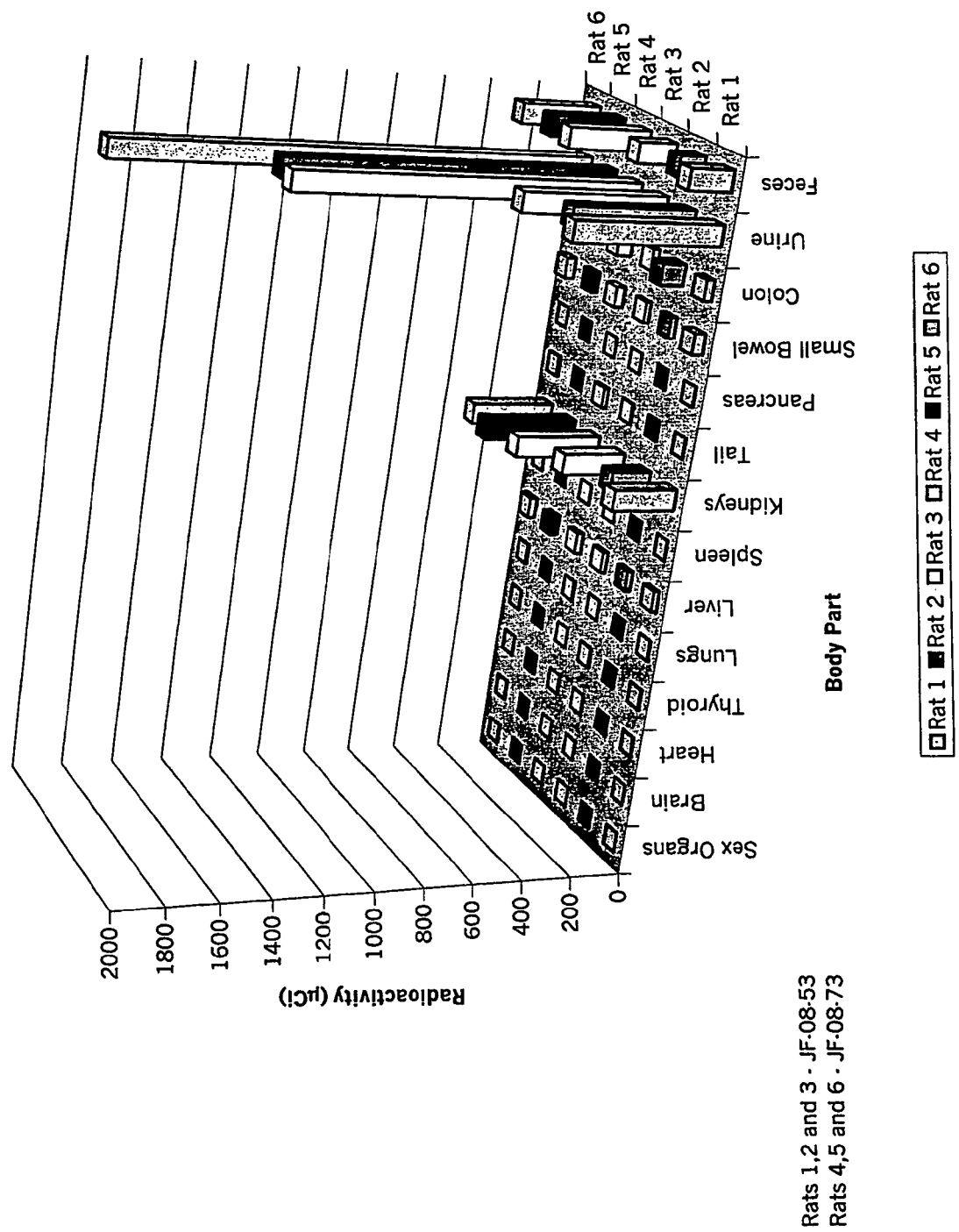
FIG. 2. is a graph displaying the biodistribution of hydrophilic peptide agents of the invention. Two $^{125}$I-labeled, hydrophilic somatostatin analogs are depicted. Note the lack of accumulation of radioactivity in normal tissue including liver, and the rapid and high efficiency elimination of the labeled peptide agents in urine and feces. Peptide JF-08-73 is $_{125}$I-succinoyl-D-Asp-D-Ser-D-Ser-D-Ser-D-Ser-D-Ser-D-Asp-D-Ser-D-Ser-D-Ser-D-Ser-D-Ser-Lys-D-Tyr-D-Tyr-cyclo[Cys-Phe-D-Trp-Lys-Thr-Cys]-Thr-NH$_2$ (SEQ ID NO: 22). Peptide JF-08-53 is $_{125}$I-D-Ser-D-Ser-D-Ser-D-Ser-D-Ser-D-Lys-D-Tyr-D-Ser-cyclo[Cys-Phe-D-Trp-Lys-Thr-Cys]-Thr-NH$_2$ (SEQ ID NO: 23).

The peptides were radiolabeled as described in Example 12. The second screw cap vial containing the highest amounts of radioactive peptide was diluted with phosphate buffered saline to achieve a final concentration of less than 3% ethanol. The solution was divided into three equal parts not exceeding 2 mL and injected intraperitoneally into each rat. Urine and feces were collected on an adsorbent pad overnight. At 24 hours, the rats were killed, dissected and each of the below organs were weighed and counted in a dose calibrator. The results are shown in FIG. 2.

EXAMPLE 20

Preparation of Thiocolchicine

Colchicine (1.25 mmole) was dissolved in 10.0 mL of water to which was added sodium methanethiolate (7.13 mmol). The yellow solution was stirred for 24 hours, then extracted 3× with ETOH:Chloroform (1:1), then evaporated to yield the desired compound as yellow crystals.

EXAMPLE 21

Preparation of Deacetylthiocolchicine

To the product from Example 1, 5.0 mL of methanol and 5.0 mL of 2N HCl were added and the solution refluxed 18 hours under dry nitrogen. The methanol was distilled off, the residual solution was reneutralized with NaOH, extracted 3 times with chloroform, evaporated, and finally lyophilized from acetonitrile/water as a yellow powder.

EXAMPLE 22

Preparation of deacetylthiocolchicine-3-thiodipropionyl-N$^\epsilon$-(2-chlorobenzyloxycarbonyl)-L-Lys-O-benzyl-D-Ser-O-benzyl-D-Ser-O-benzyl-D-Ser -O-benzyl-D-Ser-O-benzyl-D-Ser-O-benzyl-D-Ser-O-benzyl-D-Ser-O-benzyl-D-Ser-O-benzyl-D-Ser-O-benzyl-D-Ser-L-Nle-O-2,6-dichlorobenzyl-D-Tyr-O-benzyl-D-Ser-S-4-methylbenzyl-L-Cys-L-Phe-D-Trp-N$^\epsilon$-(2-chlorobenzyloxycarbonyl)-L-Lys-O-benzyl-L-Thr-S-4-methylbenzyl-L-Cys-O-benzyl-L-Thr-MBHA resin (SEQ ID NO: 39)

Methylenzhydrylamine (MBHA) polystyrene resin (Bachem, Inc., Torrance, Calif.) (0.25 mmole) was added to the reaction vessel of a CS136 automatic peptide synthesizer (CS Bio, Inc., San Carlos, Calif.) and swollen in methylene chloride (DCM) for approximately 1 hour. The resin was filtered and an excess of 10% diisopropylethylamine (DIPEA) was added and mixed for two minutes. The resin was filtered and again an excess amount of 10% DIPEA added and mixed for five minutes to ensure complete neutralization of the resin. After neutralization, the resin was washed 4 times with DCM and then the first protected amino acid, Boc-Thr(Bzl)-OH (0.75 mmol), diisopropylcarbodiimide (DIC) (0.75 mmol), and N-hydroxybenzotriazole monohydrate (HOBt) (0.75 mmol) were all dissolved in DMF and added to the resin which was mixed (1 h) followed by washing 4 times with DCM.

The tBoc group was removed by adding an excess of 40% Trifluoroacetic Acid (TFA) DCM and mixed for 2 minutes. The resin was filtered and again an excess amount of 40% TFA added and mixed for 20 minutes to ensure complete removal of the N-terminal tBoc. The resin was filtered and an excess of 10% diisopropylethylamine (DIPEA) was added and mixed for two minutes. The resin was filtered and again an excess amount of 10% DIPEA added and mixed for 5 minutes to ensure complete neutralization of the resin. After neutralization, the resin was washed 4 times with DCM and then following the same general coupling procedures, the following amino acids were successively reacted with the growing peptide chain: Boc-S-4-methylbenzyl-L-cysteine, Boc-O-benzyl-L-threonine, N$^\alpha$-Boc-N$^\epsilon$-(2-chlorobenzyloxycarbonyl)-L-lysine, Boc-D-tryptophan, Boc-L-phenylalanine, Boc-S-4-methylbenzyl-L-cysteine, Boc-O-benzyl-D-serine, Boc-O-2,6-dichlorobenzyl-D-tyrosine, Boc-norleucine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, Boc-O-benzyl-D-serine, N$^\alpha$-Boc-N$^\epsilon$-(2-chlorobenzyloxycarbonyl)-L-lysine, 3-thiodiproprionic acid, and finally without the tBoc deprotection step, deacetylthiocolchicine was coupled in DCM/Dic. The resin was finally washed 4 times with methanol and left overnight to dry.

EXAMPLE 23

Preparation of Deacetylthiocolchicine-3-thiodipropionyl-D-Ser-D-Ser-D-Ser-D-Ser -D-Ser-D-Ser-D-Ser-D-Ser-D-Ser-D-Ser-L-Norleucine-D-Tyr-D-Ser-cyclo[L-Cys-L-Phe-D-Trp-L-Lys-L-Thr-L-Cys]-L-Thr-NH$_2$ (SEQ ID NO: 40)

The peptidyl resin from Example 10 along with 5 mL of anisole was placed in a Teflon apparatus appropriate for anhydrous hydrogen fluoride manipulation. The reaction vessel was cooled in an alcohol/dry ice bath for 5 minutes and then 35 mL of gaseous anhydrous fluoride (HF) was condensed into the reaction vessel. The bath was changed from dry ice to regular ice and allowed to mix for one hour, then the HF was purged from the reaction vessel with a stream of nitrogen. The peptide was precipitated 3 times with excess ethyl ether and filtered. The filtered, crude peptide was dissolved in 60-90 percent acetic acid (250 ml). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 ml in vacuo and the crude peptide purified by preparative reverse phase high pressure liquid chromatography (RP-hplc) on a column (21.4×250 mm) of C-18 bonded silica (Dynamax 300, 8 µm). A linear gradient elution system at a flow rate of 20 mL/min was employed: buffer A consisted of 0.1% TFA and a buffer B, 0.1% TFA in 80% MeCN; 20% B to 50% B was increased at 1% per minute. The separations were monitored at 280 nm. The fractions containing the pure product as evidenced by analytical HPLC were pooled, concentrated in vacuo and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 24

Preparation of the Acyl Chloride of Camptothecin

Camptothecin (0.574 mmole) was suspended in 30 mL anhydrous DCM in a 100 mL RB flask. To this slurry, DMAP (2,455 mmole) dissolved in 20 mL anhydrous DCM was added over 20 minutes at 0° C. under a dry nitrogen atmosphere. Phosgene (0.965 mmole) was added to the slurry and mixed for 30 minutes at 0° C. and 2 hours at RT. Excess phosgene and methylene chloride were evaporated and the acyl chloride of camptothecin dissolved in metylene chloride.

EXAMPLE 25

Preparation of Camptothecin-carbonyl-Sar-D-tert-butyl-Ser-Norleucine-D-tert-butyl -Tyr-D-tert-butyl-Ser-S-trityl-Cys-Phe-D-Trp-epsilon-tert-butyloxycarbonyl-Lys-tert-butyl-Thr-S-trityl-Cys-tert-butyl-Thr-Rink-amide-resin (SEQ ID NO: 41)

Rink amide MBHA polystyrene resin (0.063 mmole) [4-(2',4'-dimethoxyphenyl-Fmoc-(aminomethyl)phenoxyacetamido-norleucyl-methylbenzhydrylamine resin, 100-200 mesh, Novabiochem, San Diego, C] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Thr(tBut) (0.188 mmol), diisopropylcarbodiimide (DIC) (0.188 mmol), and N-hydroxybenxotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-t-butyl-L-threonine-$N^\alpha$-Fmoc-$N^\epsilon$-Boc-L-lysine, $N^\alpha$-Fmoc-$N^{in}$-Boc-D-tryptophan, Fmoc-L-phenylalanine, Fmoc-S-trityl-L-cysteine, Fmoc-O-t-butyl-D-serine, Fmoc-O-t-butyl-D-tyrosine, $N^\alpha$-Fmoc-norleucine, Fmoc-O-t-butyl-D-serine, Fmoc-sarcosine. After removal of the final Fmoc group, Camptothecin acyl chloride from EXAMPLE 24 was added to the resin and mixed overnight, washed with copious amounts of DMF followed by DCM then methanol. After a final filtration the derivatized resin air dried overnight.

EXAMPLE 26

Preparation of camptothecin-carbonyl-Sar-D-Ser-Nle-D-Tyr-D-Ser-cyclo[Cys-Phe-D-Trp-Lys-Thr-Cys]-Thr-amide (SEQ ID NO: 30)

The camptothecin-peptide resin prepared in Example 25 (0.063 mmol) was placed in a round bottomed flask to which was added 15 ml of a solution of trifluoroacetic acid (TFA) containing water (2.5%), 1,2-ethanedithiol (2.5%), and triisopropylsilane (1%). The suspension was agitated (2 h), filtered, and washed several times with TFA. The TFA was evaporated in vacuo and ether added to the resulting oil to give a yellow powder which was then dissolved in 60% acetic acid (250 ml). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 ml in vacuo and the crude camptothecin peptide purified by preparative reverse phase high pressure liquid chromatography (RP-hplc) on a column (21.4×250 mm) of C-18 bonded silica (Dynamax 300, 8 μm). A linear gradient elution system at a flow rate of 20 mL/min was employed: buffer A consisted of 0.1% TFA and buffer B, 0.1% TFA in 80% MeCN; 20% B to 50% B was increased at 1% per min. The separation were monitored at 280 nm. The fractions containing the pure product as evidenced by analytical hplc were pooled, concentrated in vacuo, and subjected to lyphilization. The peptide was obtained as a fluffy white powder of constant weight by lyphilization from aqueous acetic acid. Correct composition was demonstrated by amino acid analysis of an acid hydrolysate and matrix assisted laser desporption mass spectrometry.

TABLE 1

Ability of various somatostatin analog conjugates to inhibit GH release from primary cultures of rat pituitary cells. For comparison, natural somatostatin-14 has an $IC_{50}$ value of 0.15 nM (ND = not done).

| Peptide | Synthesis Code | $IC_{50}$ (nM) |
|---|---|---|
| Somatostatin-14 | | 0.15 |
| JF-07-100 | | 0.62 |
| JF-08-87A | | 0.16 |
| JF-09-35 | | ND |
| D-Ser-D-Ser-D-Ser-D-Ser-D-Ser-L-Lys-D-Tyr-D-Tyr-cyclo[L-Cys-L-Phe-L-Trp-L-Lys-L-Thr-L-Cys]-L-Thr-$NH_2$ | (SEQ ID NO: 27) | 0.14 |
| D-Ser-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-$NH_2$ | (SEQ ID NO: 38) | 0.12 |
| Acetyl-D-Ser-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-$NH_2$ | (SEQ ID NO: 38) | 0.57 |
| D-Ser-D-Ser-D-Ser-D-Ser-D-Ser-L-Lys-D-Ser-D-Ser-cyclo[L-Cys-L-Phe-D-Trp-L-Lys-L-Thr-L-Cys]-L-Thr-$NH_2$ | (SEQ ID NO: 42) | 3.29 |
| DOTA-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-$NH_2$ | (SEQ ID NO: 38) | 0.71 |
| D-Ser-D-Ser-D-Ser-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-$NH_2$ | (SEQ ID NO: 43) | 0.32 |
| D-Ser-D-Ser-D-Ser-D-Ser-D-Ser-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-$NH_2$ | (SEQ ID NO: 44) | ND |
| D-Ser-D-Ser-D-Ser-D-Ser-D-Ser-D-Ser-L-Lys-D-Tyr-D-Ser-cyclo[L-Cys-L-Phe-D-Trp-L-Lys-L-Thr-L-Cys]-L-Thr-$NH_2$ | (SEQ ID NO: 23) | 0.086 |
| D-Gln-D-Gln-D-Gln-D-Gln-D-Gln-D-Gln-D-Gln-D-Gln-D-Gln-D-Gln-L-Lys-D-Tyr- | (SEQ ID NO: 45) | 0.24 |

TABLE 1-continued

Ability of various somatostatin analog conjugates to inhibit GH release from primary cultures of rat pituitary cells. For comparison, natural somatostatin-14 has an $IC_{50}$ value of 0.15 nM (ND = not done).

| Peptide | Synthesis Code | $IC_{50}$ (nM) |
|---|---|---|
| D-Tyr-cyclo[L-Cys-L-Phe-D-Trp-L-Lys-L-Thr-L-Cys]-L-Thr-NH$_2$ | | |
| 3-N,N-Dimethylaminobenzoic-D-Ser-D-Ser-D-Ser-D-Ser-D-Ser-D-Ser-D-Ser-D-Ser-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-NH$_2$ | (SEQ ID NO: 46) | 0.27 |
| Succinate-D-Asp-D-Ser-D-Ser-D-Ser-D-Ser-D-Ser-D-Asp-D-Ser-D-Ser-D-Ser-D-Ser-L-Lys-D-Tyr-D-Tyr-cyclo[L-Cys-L-Phe-D-Trp-L-Lys-L-Thr-L-Cys]-L-Thr-NH$_2$ | (SEQ ID NO: 22) | 0.51 |
| D-Ser-D-Ser-D-Ser-D-Ser-D-Ser-L-Norleucine-D-Tyr-D-Ser-cyclo[L-Cys-L-Phe-D-Trp-L-Lys-L-Thr-L-Cys]-L-Thr-NH$_2$ | (SEQ ID NO: 21) | 0.094 |
| D-Ser-D-Ser-D-Ser-D-Ser-D-Ser-L-4Pal-D-Tyr-D-Ser-cyclo[L-Cys-L-Phe-D-Trp-L-Lys-L-Thr-L-Cys]-L-Thr-NH$_2$ | (SEQ ID NO: 47) | 0.18 |
| D-Ser-D-Ser-D-Ser-D-Ser-D-Ser-L-Gln-D-Tyr-D-Ser-cyclo[L-Cys-L-Phe-D-Trp-L-Lys-L-Thr-L-Cys]-L-Thr-NH$_2$ | (SEQ ID NO: 48) | 0.45 |
| D-Ser-D-Ser-D-Ser-D-Ser-D-Ser-L-Asp-D-Tyr-D-Ser-cyclo[L-Cys-L-Phe-D-Trp-L-Lys-L-Thr-L-Cys]-L-Thr-NH$_2$ | (SEQ ID NO: 49) | 7.55 |
| Succinate-D-Asp-D-Ser-D-Ser-D-Ser-D-Ser-D-Ser-L-Norleucine-D-Tyr-D-Ser-cyclo[L-Cys-L-Phe-D-Trp-L-Lys-L-Thr-L-Cys]-L-Thr-NH$_2$ | (SEQ ID NO: 50) | 0.52 |
| Succinate-D-Ser-D-Ser-D-Ser-D-Ser-D-Ser-L-Ser-D-Tyr-D-Ser-cyclo[L-Cys-L-Phe-D-Trp-L-Lys-L-Thr-L-Cys]-L-Thr-NH$_2$ | (SEQ ID NO: 51) | 5.6 |
| Succinate-D-Ser-D-Ser-D-Ser-D-Ser-D-Ser-D-Ser-L-2-Aminobutyric acid-D-Tyr-D-Ser-cyclo[L-Cys-L-Phe-D-Trp-L-Lys-L-Thr-L-Cys]-L-Thr-NH$_2$ | (SEQ ID NO: 52) | 0.61 |
| D-Ser-D-Ser-D-Ser-D-Ser-D-Ser-L-Thr-D-Tyr-D-Ser-cyclo[L-Cys-L-Phe-D-Trp-L-Lys-L-Thr-L-Cys]-L-Thr-NH$_2$ | (SEQ ID NO: 53) | 0.72 |
| Succinate-D-Asp-D-Ser-D-Ser-D-Ser-D-Ser-D-Ser-L-Thr-D-Tyr-D-Ser-cyclo[L-Cys-L-Phe-D-Trp-L-Lys-L-Thr-L-Cys]-L-Thr-NH$_2$ | (SEQ ID NO: 54) | 5.17 |
| D-Ser-D-Ser-D-Ser-D-Ser-D-Ser-L-hSer-D-Tyr-D-Ser-cyclo[L-Cys-L-Phe-D-Trp-L-Lys-L-Thr-L-Cys]-L-Thr-NH$_2$ | (SEQ ID NO: 55) | 0.55 |
| Mercaptoacetate-Gly-Gly-D-Asp-D-Ser-D-Ser-D-Ser-D-Ser-D-Ser-L-4Pal-D-Tyr-D-Ser-cyclo[L-Cys-L-Phe-D-Trp-L-Lys-L-Thr-L-Cys]-L-Thr-NH$_2$ | (SEQ ID NO: 56) | 0.97 |
| D-Ser-D-Ser-D-Ser-D-Gln-D-Ser-D-Ser-D-Ser-D-Gln-D-Ser-D-Ser-D-Ser-D-Gln-L-Norvaline-D-Tyr-D-Ser-cyclo[L-Cys-L-Phe-D-Trp-L-Lys-L-Thr-L-Cys]-L-Thr-NH$_2$ | (SEQ ID NO: 57) | 0.93 |
| D-Ser-L-Ser-D-Ser-L-Ser-D-Ser-L-Ser-D-Ser-L-Ser-D-Ser-L-2-Aminobutyric acid-D-Tyr-D-Ser-cyclo[L-Cys-L-Phe-D-Trp-L-Lys-L-Thr-L-Cys]-L-Thr-NH$_2$ | (SEQ ID NO: 58) | ND |

OTHER EMBODIMENTS

Although the present invention has been described with reference to preferred embodiments, one skilled in the art can easily ascertain its essential characteristics and, without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications, patents, and applications mentioned in the specification are herein incorporated by reference.

We claim:

1. A peptide agent having the formula:

X-Y-Z-Q, wherein:

X is selected from the group consisting of cytotoxic agents, therapeutic agents, detectable labels, and chelating groups;
Y is a peptide that increases the hydrophilic biodistribution of said agent, a hydrophilic polymer that includes a linker for X, or is omitted;
Q is a somatostatin peptide or analog thereof having biological activity; and
Z is D-Ser-Nle-D-Tyr-D-Ser-c[Cys-Phe-D-Trp-Lys-Thr-Cys]-Thr-$NH_2$, a linking peptide that, when bonded to Q at the N-terminus or at a compatible side-chain amino group of Q, preserves at least 50% of the biological activity of Q.

2. A peptide agent having the formula:

X-Y-Z-Q, wherein:

X is a cytotoxic agent or a therapeutic agent;
Y is a peptide that increases the hydrophilic biodistribution of said agent, a hydrophilic polymer that includes a linker for X, or is omitted;
Q is a somatostatin peptide having biological activity; and
Z is D-Ser-Nle-D-Tyr-D-Ser-c[Cys-Phe-D-Trp-Lys-Thr-Cys]-Thr-$NH_2$, a linking peptide that, when bonded to Q at the N-terminus or at a compatible side-chain amino group of Q, preserves at least 50% of the biological activity of Q.

3. The peptide agent of claim 2, wherein Y is a peptide that increases the hydrophilic biodistribution of said agent.

4. The peptide agent of claim 3, wherein Y is of the formula:

$U(V-V)_n$, wherein:

U is D-Pro, L-Pro, D-4-OH-Pro, L-4-OH-Pro, Sar, or ($NH_2$—$(CH_2)_m$—COOH) where m=2-10, inclusive, or is deleted;
each V is independently selected from the group consisting of: D-Ser, L-Ser, D-Thr, L-Thr, D-Gln, L-Gln, D-Asn, L-Asn, D-4-OH-Pro, and L-4-OH-Pro; and
n is an integer from 1 to 50, inclusive.

5. The peptide agent of claim 4, wherein each V is independently D-Ser or L-Ser.

6. The peptide agent of claim 2, wherein Y is a hydrophilic polymer.

7. The peptide agent of claim 6, wherein Y is polyethylene glycol, polyvinyl acetate, polyvinyl alcohol, HPMA (N-(2-hydroxypropyl)methacrylamide) or HPMA copolymers, α,β-poly(N-hydroxyethyl)-DL-aspartamide (PHEA), or α,β-poly(N-hydroxypropyl)-DL-aspartamide.

8. The peptide agent of claim 2, wherein X is a cytotoxic agent.

9. The peptide agent of claim 8, wherein X is an antimetabolic agent.

10. The peptide agent of claim 8, wherein X is a methotrexate.

11. The peptide agent of claim 8, wherein X is selected from the group consisting of the following compounds and their derivatives: doxorubicin, methotrexate, camptothecin, homocamptothecins, rhizoxins, dolistatins, paclitaxol, and maytansinoids.

12. The peptide agent of claim 2, wherein Q is a somatostatin analog.

13. A peptide agent having the formula:

X-Y-Z-Q, wherein:

X is selected from the group consisting of a detectable label and a chelating group;
Y is a peptide that increases the hydrophilic biodistribution of said agent, a hydrophilic polymer that includes a linker for X, or is omitted;
Q is a somatostatin peptide or analog thereof having biological activity; and
Z is D-Ser-Nle-D-Tyr-D-Ser-c[Cys-Phe-D-Trp-Lys-Thr-Cys]-Thr-$NH_2$, a linking peptide that, when bonded to Q at the N-terminus or at a compatible side-chain amino group of Q, preserves at least 50% of the said biological activity of Q.

14. The peptide agent of claim 13, wherein said peptide agent is attached to a detectable label.

15. The peptide agent of claim 14, wherein said peptide agent is indirectly attached to a detectable label.

16. The peptide agent of claim 14, wherein said peptide agent is directly attached to a detectable label.

17. The peptide agent of claim 14, wherein said detectable label is radioactive.

18. The peptide agent of claim 17, wherein said detectable label is an iodine, astatine, or bromine label that is attached to an amino acid of said peptide agent.

19. The peptide agent of claim 13, wherein X is a chelating group.

20. The peptide agent of claim 13, wherein X is omitted, and Y is lower acetylated, succinylated, maleinylated, or fumarylated.

21. The peptide agent of claim 13, wherein Y is a peptide sequence that increases the hydrophilic biodistribution of said agent.

22. The peptide agent of claim 21, wherein Y is of the formula:

$U(V-V)_n$, wherein:

U is D-Pro, L-Pro, D-4-OH-Pro, L-4-OH-Pro, Sar, or ($NH_2$—$(CH_2)_m$—COOH) where m=2-10, inclusive, or is deleted;
each V is independently selected from the group consisting of: D-Ser, L-Ser, D-Thr, L-Thr, D-Gln, L-Gln, D-Asn, L-Asn, D-4-OH-Pro, and L-4-OH-Pro; and
n is an integer from 1 to 50, inclusive.

23. The peptide agent of claim 22, wherein each V is independently D-Ser, L-Ser, or D-Gln.

24. The peptide agent of claim 13, wherein Y is a hydrophilic polymer.

25. The peptide agent of claim 24, wherein Y is polyethyleneglycol, PHEA, or polyvinylalcohol.

26. The peptide agent of claim 13, wherein Q is a somatostatin analog.

27. The peptide agent of claim 4, wherein at least one V is a D-amino acid.

28. The peptide agent of claim 22, wherein at least one V is a D-amino acid.

29. The peptide agent of claim 19, wherein said chelating group comprises an isotope of Lu, In, Y, or Sm.

* * * * *

UNITED STATES PATENT AND TRADEMARK OFFICE
CERTIFICATE OF CORRECTION

PATENT NO.       : 7,326,685 B2                                          Page 1 of 3
APPLICATION NO.  : 10/490326
DATED            : February 5, 2008
INVENTOR(S)      : Coy et al.

It is certified that error appears in the above-identified patent and that said Letters Patent is hereby corrected as shown below:

Column 3, Line 67, replace "dolistatins" with --dolastatins--.

Column 4,
    Line 6, replace "dolistatins" with --dolastatins--.

Column 6, Line 25, replace "cytoxic" with --cytotoxic--.

Column 8,
    Line 56, replace "hydroxyelthyl" with --hydroxyethyl--.
    Line 57, replace "polysuccinamide (PSI)," with
    --polysuccinimide (PSI),--.

Column 9,
    Line 27, replace "$_{125}$I-succinoyl-" with --$^{125}$I-succinoyl- --.
    Line 30, replace "$_{125}$I-" with --$^{125}$I- --.

Column 10, Line 8, replace "respecitively," with --respectively--.

Column 11, Line 52, replace "cyctotoxic" with --cytotoxic--.

Column 12,
    Line 9, replace "cytoxic" with --cytotoxic--.
    Line 25, replace "A. metantrone" with --Ametantrone--.
    Line 65, replace "PeploycinSulfate" with --Peploycin
    Sulfate--.

Column 13,
    Line 26, replace "mechlor ethamine" with --mechlorethamine--.
    Line 27, replace "N-methyl-Nnitrosourea (MUN)" with --N-methyl-N-nitrosourea (MUN)--.
    Line 33, replace "diacarbazine" with --dacarbazine--.
    Line 57, replace "argininedeaminase" with --arginine deaminase--.

Signed and Sealed this

Twenty-seventh Day of July, 2010

David J. Kappos
*Director of the United States Patent and Trademark Office*

CERTIFICATE OF CORRECTION (continued)
U.S. Pat. No. 7,326,685 B2

Column 14,
    Line 46, replace "rnerbarone" with --merbarone--.
    Line 62, replace "ondansetron; ondansetron;" with --ondansetron;--.
    Line 65, replace "palauamine" with --palau amine--.

Column 15,
    Line 8, replace "protein kinase C inhibitor; protein kinase C inhibitors;" with --protein kinase C inhibitors;--.
    Line 54, replace "lobenguane" with --Iobenguane--.
    Line 56, replace "lodohippurate" with --Iodohippurate--.
    Line 58, replace "lofetamine" with --Iofetamine--.

Column 18,
    Line 11, replace "ininocarboxylic" with --aminocarboxylic--.
    Line 52, replace "administed" with --administered--.

Column 19, Line 43, replace "naphalenes" with --naphthalenes--.

Column 29,
    Line 14, replace "Methylenzhydrylamine" with --Methylbenzhydrylamine--.
    Line 67, replace "manupulation" with --manipulation--.

Column 30, Line 45, replace "metylene" with --methylene--.

Column 31,
    Line 63, replace "lyphilization" with --lyophilization--.
    Line 66, replace "desporption" with --desorption--.

Column 63,
    Line 11, in claim 1, replace "Q is a somatostatin peptide" with --Q is c[Cys-Phe-D-Trp-Lys-Thr-Cys]-Thr-NH$_2$, a somatostatin peptide--.
    Line 13, in claim 1, replace "Z is D-Ser-Nle-D-Tyr-D- Se c[Cys-Phe-D-Trp-Lys-Thr-Cys]-Thr-NH$_2$, a linking peptide" with --Z is D-Ser-Nle-D-Tyr-D-Ser, a linking peptide--.
    Line 25, in claim 2, replace "Q is a somatostatin peptide" with --Q is c[Cys-Phe-D-Trp-Lys-Thr-Cys]-Thr-NH$_2$, a somatostatin peptide--.
    Line 26, in claim 2, replace "Z is D-Ser-Nle-D-Tyr-D-Ser-c[Cys-Phe-D-Trp-Lys-Thr-Cys]-Thr-NH$_2$, a linking peptide" with --Z is D-Ser-Nle-D-Tyr-D-Ser, a linking peptide--.

Column 63,
    Line 61, in claim 11, replace "dolistatins" with
--dolistatin--.

Column 64,
    Line 11, in claim 13, replace "Q is a somatostatin peptide"
with --Q is c[Cys-Phe-D-Trp-Lys-Thr-Cys]-Thr-$NH_2$, a
somatostatin peptide--.
    Line 13, in claim 13, replace "Z is D-Ser-Nle-D-Tyr-D-
Ser-c[Cys-Phe-D-Trp-Lys-Thr-Cys]-Thr-$NH_2$,
a linking peptide" with --Z is D-Ser-Nle-D-Tyr-D-Ser, a linking peptide--.

SEQUENCE LISTING

<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Lys, Tyr, Ser, or is absent
<220> FEATURE:
<221> NAME/KEY: VARIANT
<222> LOCATION: 2
<223> OTHER INFORMATION: Xaa = Lys, Tyr or is absent
<220> FEATURE:
<221> NAME/KEY: VARIANT
<222> LOCATION: 3
<223> OTHER INFORMATION: Xaa = Lys, Ser, hSer, Thr, Nle, 4Abu, Nva, Pal,
      Orn, Dab, Dap, Phe, OH-Pro or  is absent
<220> FEATURE:
<221> NAME/KEY: VARIANT
<222> LOCATION: 4
<223> OTHER INFORMATION: Xaa = Lys, Tyr, Ser, OH-Pro, iodo-Tyr,
      diiodo-Tyr, astatine-Tyr, bromo-Tyr, dibromo-Tyr, Asn, Asp, Glu or
      Gln
<221> NAME/KEY: VARIANT
<222> LOCATION: 5
<223> OTHER INFORMATION: Xaa = Lys, Tyr, Ser, OH-Pro, iodo-Tyr,
      diiodo-Tyr, astatine-Tyr, bromo-Tyr, dibromo-Tyr, Asn, Asp, Glu,
      Gln
<220> FEATURE:
<223> OTHER INFORMATION: Synthetic

<400> SEQUENCE: 1

Xaa Xaa Xaa Xaa Xaa
 1               5

<210> SEQ ID NO 2
<211> LENGTH: 4
<212> TYPE: PRT
<213> ORGANISM: Artificial Sequence
<220> FEATURE:
<221> NAME/KEY: VARIANT
<222> LOCATION: 2
<223> OTHER INFORMATION: Xaa = Nle
<220> FEATURE:
<223> OTHER INFORMATION: Synthetic

<400> SEQUENCE: 2

Ser Xaa Ser Ser
 1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Ser Lys Ser Ser
 1

<210> SEQ ID NO 4
<211> LENGTH: 4
<212> TYPE: PRT
<213> ORGANISM: Artificial Sequence
<220> FEATURE:
<223> OTHER INFORMATION: Synthetic

```
-continued

<400> SEQUENCE: 4

Ser Lys Tyr Tyr
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Ser Lys Tyr Ser
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Ser Ser Lys Ser
1

<210> SEQ ID NO 7
<211> LENGTH: 4
<212> TYPE: PRT
<213> ORGANISM: Artificial Sequence
<220> FEATURE:
<221> NAME/KEY: VARIANT
<222> LOCATION: 2
<223> OTHER INFORMATION: Xaa = Nle
<220> FEATURE:
<223> OTHER INFORMATION: Synthetic

<400> SEQUENCE: 7

Ser Xaa Tyr Ser
1

<210> SEQ ID NO 8
<211> LENGTH: 4
<212> TYPE: PRT
<213> ORGANISM: Artificial Sequence
<220> FEATURE:
<221> NAME/KEY: VARIANT
<222> LOCATION: 2
<223> OTHER INFORMATION: Xaa = Pal
<220> FEATURE:
<223> OTHER INFORMATION: Synthetic

<400> SEQUENCE: 8

Ser Xaa Tyr Ser
1

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Ser Thr Tyr Ser
1
```

```
<210> SEQ ID NO 10
<211> LENGTH: 3
<212> TYPE: PRT
<213> ORGANISM: Artificial Sequence
<220> FEATURE:
<223> OTHER INFORMATION: Synthetic

<400> SEQUENCE: 10

Lys Ser Ser
 1

<210> SEQ ID NO 11
<211> LENGTH: 3
<212> TYPE: PRT
<213> ORGANISM: Artificial Sequence
<220> FEATURE:
<223> OTHER INFORMATION: Synthetic

<400> SEQUENCE: 11

Ser Lys Ser
 1

<210> SEQ ID NO 12
<211> LENGTH: 3
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Nle
<220> FEATURE:
<223> OTHER INFORMATION: Synthetic

<400> SEQUENCE: 12

Xaa Tyr Ser
 1

<210> SEQ ID NO 13
<211> LENGTH: 3
<212> TYPE: PRT
<213> ORGANISM: Artificial Sequence
<220> FEATURE:
<223> OTHER INFORMATION: Synthetic

<400> SEQUENCE: 13

Lys Tyr Ser
 1

<210> SEQ ID NO 14
<211> LENGTH: 3
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Pal
<220> FEATURE:
<223> OTHER INFORMATION: Synthetic

<400> SEQUENCE: 14

Xaa Lys Ser
 1

<210> SEQ ID NO 15
<211> LENGTH: 3
<212> TYPE: PRT
<213> ORGANISM: Artificial Sequence
<220> FEATURE:
<223> OTHER INFORMATION: Synthetic
```

```
<400> SEQUENCE: 15

Thr Tyr Ser
1

<210> SEQ ID NO 16
<211> LENGTH: 3
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Lys, Orn, Dab, Dap, Phe, Nle, Ser, hSer,
      Abu, Nva, OH-Pro, or is absent
<220> FEATURE:
<221> NAME/KEY: VARIANT
<222> LOCATION: 2
<223> OTHER INFORMATION: Xaa = Lys, Tyr, Ser, OH-Pro, iodo-Tyr,
      diiodo-Tyr, bromo-Tyr, dibromo-Tyr, Asn, Asp, or Glu
<221> NAME/KEY: VARIANT
<222> LOCATION: 3
<223> OTHER INFORMATION: Xaa = Lys, Tyr, Ser, OH-Pro, iodo-Tyr,
      diiodo-Tyr, bromo-Tyr, dibromo-Tyr, Asn, Asp, or Glu
<220> FEATURE:
<223> OTHER INFORMATION: Synthetic

<400> SEQUENCE: 16

Xaa Xaa Xaa
1

<210> SEQ ID NO 17
<211> LENGTH: 3
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Lys, Orn, Dab, Dap, Phe, Nle, Ser, hSer,
      Abu, Nva, OH-Pro, or is absent
<220> FEATURE:
<223> OTHER INFORMATION: Synthetic

<400> SEQUENCE: 17

Xaa Tyr Ser
1

<210> SEQ ID NO 18
<211> LENGTH: 3
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Pro, OH-Pro, Sar, Lys, Orn, Dab, Dap, or
      Phe
<220> FEATURE:
<221> NAME/KEY: VARIANT
<222> LOCATION: 2
<223> OTHER INFORMATION: Xaa = Ser, Thr, Gln, Asn,  or OH-Pro
<221> NAME/KEY: VARIANT
<222> LOCATION: 3
<223> OTHER INFORMATION: Xaa = Ser, Thr, Gln, Asn, or OH-Pro
<220> FEATURE:
<223> OTHER INFORMATION: Synthetic

<400> SEQUENCE: 18

Xaa Xaa Xaa
1

<210> SEQ ID NO 19
<211> LENGTH: 3
```

```
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Pro, OH-Pro, Sar, Lys, Orn, Dab, Dap, or
      Phe
<220> FEATURE:
<223> OTHER INFORMATION: Synthetic

<400> SEQUENCE: 19

Xaa Ser Ser
 1

<210> SEQ ID NO 20
<211> LENGTH: 9
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Gln, Asn, Nle, or Nva.
<220> FEATURE:
<221> NAME/KEY: VARIANT
<222> LOCATION: 3
<223> OTHER INFORMATION: Xaa = Ava, Gly, Leu, Val, Ile, Nle, or Nva.
<220> FEATURE:
<221> NAME/KEY: VARIANT
<222> LOCATION: 4
<223> OTHER INFORMATION: Xaa = BAla, 4-aminobutyric acid, Gly, Ala,
      D-Ala, N-Me-Ala, or N-ME-D-Ala.
<220> FEATURE:
<221> NAME/KEY: VARIANT
<222> LOCATION: 6
<223> OTHER INFORMATION: Xaa = Phe, Tyr, 4-Chloro-Phe, 4-Fluoro-Phe,
      4-Bromo-Phe, 4-NO2-Phe, Ala, Gly, Leu, Val, Ile,
      Nle, or Nva.
<220> FEATURE:
<221> NAME/KEY: VARIANT
<222> LOCATION: 7
<223> OTHER INFORMATION: Xaa = Met, Phe, Tyr, 4-Chloro-Phe,
      4-Fluoro-Phe, 4-Bromo-Phe, 4-NO2-Phe, Ala, Gly, Leu, Val, Ile,
      Nle, or Nva.
<220> FEATURE:
<221> NAME/KEY: VARIANT
<222> LOCATION: 8
<223> OTHER INFORMATION: Xaa = Ava, Gly, Leu, Val, Ile, Nle, or Nva.
<221> NAME/KEY: VARIANT
<222> LOCATION: (9)...(9)
<223> OTHER INFORMATION: Xaa = Ava, Gly, Leu, Val, Ile, Nle, or Nva.
<220> FEATURE:
<223> OTHER INFORMATION: synthetic

<400> SEQUENCE: 20

Xaa Trp Xaa Xaa His Xaa Xaa Xaa Xaa
 1               5

<210> SEQ ID NO 21
<211> LENGTH: 15
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = Nle
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 21

Ser Ser Ser Ser Ser Xaa Tyr Ser Cys Phe Trp Lys Thr Cys Thr
 1               5                  10                  15
```

```
<210> SEQ ID NO 22
<211> LENGTH: 22
<212> TYPE: PRT
<213> ORGANISM: Artificial Sequence
<220> FEATURE:
<221> NAME/KEY: MOD_RES
<222> LOCATION: 16, 21
<223> OTHER INFORMATION: Cys at positions 16 and 21 are circularized
<220> FEATURE:
<223> OTHER INFORMATION: Synthetic

<400> SEQUENCE: 22

Asp Ser Ser Ser Ser Ser Asp Ser Ser Ser Ser Lys Tyr Tyr Cys
 1               5                  10                  15

Phe Trp Lys Thr Cys Thr
            20

<210> SEQ ID NO 23
<211> LENGTH: 15
<212> TYPE: PRT
<213> ORGANISM: Artificial Sequence
<220> FEATURE:
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 23

Ser Ser Ser Ser Ser Lys Tyr Ser Cys Phe Trp Lys Thr Cys Thr
 1               5                  10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Lys Tyr Lys Tyr Lys Cys Phe Trp Lys Thr Cys Thr
 1               5                  10

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Ser Ser Ser Ser Ser Lys Tyr Tyr Cys Phe Trp Lys Thr Cys Thr
 1               5                  10                  15

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Leu Ala Leu Ala Ser Ser Ser Ser Ser Lys Tyr Ser Cys Phe Trp Lys
 1               5                  10                  15

Thr Cys Thr
```

<210> SEQ ID NO 27
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 9, 14
<223> OTHER INFORMATION: Cys at positions 9 and 14 are circularized

<400> SEQUENCE: 27

Ser Ser Ser Ser Ser Lys Tyr Tyr Cys Phe Trp Lys Thr Cys Thr
1               5                   10                  15

<210> SEQ ID NO 28
<211> LENGTH: 18
<212> TYPE: PRT
<213> ORGANISM: Artificial Sequence
<220> FEATURE:
<221> NAME/KEY: VARIANT
<222> LOCATION: 15
<223> OTHER INFORMATION: Xaa = BAla
<221> NAME/KEY: VARIANT
<222> LOCATION: 18
<223> OTHER INFORMATION: Xaa = Nle
<220> FEATURE:
<223> OTHER INFORMATION: Synthetic

<400> SEQUENCE: 28

Ser Ser Ser Ser Ser Ser Ser Ser Tyr Ser Gln Trp Ala Val Xaa His
1               5                   10                  15

Phe Xaa

<210> SEQ ID NO 29
<211> LENGTH: 21
<212> TYPE: PRT
<213> ORGANISM: Artificial Sequence
<220> FEATURE:
<221> NAME/KEY: VARIANT
<222> LOCATION: 12
<223> OTHER INFORMATION: Xaa = Nle
<221> NAME/KEY: MOD_RES
<222> LOCATION: 15, 20
<223> OTHER INFORMATION: Cys at positions 15 and 20 are circularized
<220> FEATURE:
<223> OTHER INFORMATION: Synthetic

<400> SEQUENCE: 29

Lys Ser Ser Ser Ser Ser Ser Ser Ser Ser Ser Xaa Tyr Ser Cys Phe
1               5                   10                  15

Trp Lys Thr Cys Thr
            20

<210> SEQ ID NO 30
<211> LENGTH: 12
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Sar
<220> FEATURE:
<221> NAME/KEY: VARIANT
<222> LOCATION: 3
<223> OTHER INFORMATION: Xaa = Nle
<221> NAME/KEY: MOD_RES
<222> LOCATION: 6, 11
<223> OTHER INFORMATION: Cys at positions 6 and 11 are circularized
<220> FEATURE:

<223> OTHER INFORMATION: Synthetic

<400> SEQUENCE: 30

Xaa Ser Xaa Tyr Ser Cys Phe Trp Lys Thr Cys Thr
 1               5                  10

<210> SEQ ID NO 31
<211> LENGTH: 12
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = Nle
<221> NAME/KEY: MOD_RES
<222> LOCATION: 6, 11
<223> OTHER INFORMATION: Cys at positions 6 and 11 are circularized
<220> FEATURE:
<223> OTHER INFORMATION: Synthetic

<400> SEQUENCE: 31

Pro Ser Xaa Tyr Ser Cys Phe Trp Lys Thr Cys Thr
 1               5                  10

<210> SEQ ID NO 32
<211> LENGTH: 12
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = OH-Pro
<220> FEATURE:
<221> NAME/KEY: VARIANT
<222> LOCATION: 3
<223> OTHER INFORMATION: Xaa = Nle
<221> NAME/KEY: MOD_RES
<222> LOCATION: 6, 11
<223> OTHER INFORMATION: Cys at positions 6 and 11 are circularized
<220> FEATURE:
<223> OTHER INFORMATION: Synthetic

<400> SEQUENCE: 32

Xaa Ser Xaa Tyr Ser Cys Phe Trp Lys Thr Cys Thr
 1               5                  10

<210> SEQ ID NO 33
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 1, 6
<223> OTHER INFORMATION: Cys at positions 1 and 6 are circularized

<400> SEQUENCE: 33

Cys Phe Trp Lys Thr Cys
 1               5

<210> SEQ ID NO 34
<211> LENGTH: 7
<212> TYPE: PRT
<213> ORGANISM: Artificial Sequence
<220> FEATURE:
<221> NAME/KEY: MOD_RES
<222> LOCATION: 1, 6
<223> OTHER INFORMATION: Cys at positions 1 and 6 are circularized
<220> FEATURE:
<223> OTHER INFORMATION: Synthetic

```
<400> SEQUENCE: 34

Cys Phe Trp Lys Thr Cys Thr
1               5

<210> SEQ ID NO 35
<211> LENGTH: 15
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = Nle
<220> FEATURE:
<223> OTHER INFORMATION: Synthetic

<400> SEQUENCE: 35

Ser Ser Ser Ser Ser Xaa Tyr Ser Cys Phe Trp Lys Thr Cys Thr
1               5                   10                  15

<210> SEQ ID NO 36
<211> LENGTH: 15
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = Nle
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 36

Ser Ser Ser Ser Ser Xaa Tyr Ser Cys Phe Trp Lys Thr Cys Thr
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: Synthetic

<400> SEQUENCE: 37

Ser Ser Ser Ser Ser Ser Ser Ser Ser Ser Lys Tyr Tyr Cys Phe Trp
1               5                   10                  15

Lys Thr Cys Thr
            20

<210> SEQ ID NO 38
<211> LENGTH: 20
<212> TYPE: PRT
<213> ORGANISM: Artificial Sequence
<220> FEATURE:
<221> NAME/KEY: MOD_RES
<222> LOCATION: 14, 19
<223> OTHER INFORMATION: Cys at positions 14 and 19 are circularized
<220> FEATURE:
<223> OTHER INFORMATION: Synthetic

<400> SEQUENCE: 38

Ser Ser Ser Ser Ser Ser Ser Ser Ser Ser Lys Tyr Tyr Cys Phe Trp
1               5                   10                  15

Lys Thr Cys Thr
            20
```

```
<210> SEQ ID NO 39
<211> LENGTH: 21
<212> TYPE: PRT
<213> ORGANISM: Artificial Sequence
<220> FEATURE:
<221> NAME/KEY: VARIANT
<222> LOCATION: 12
<223> OTHER INFORMATION: Xaa = Nle
<220> FEATURE:
<223> OTHER INFORMATION: Synthetic

<400> SEQUENCE: 39

Lys Ser Ser Ser Ser Ser Ser Ser Ser Ser Xaa Tyr Ser Cys Phe
1               5                   10                  15

Trp Lys Thr Cys Thr
            20

<210> SEQ ID NO 40
<211> LENGTH: 20
<212> TYPE: PRT
<213> ORGANISM: Artificial Sequence
<220> FEATURE:
<221> NAME/KEY: VARIANT
<222> LOCATION: 11
<223> OTHER INFORMATION: Xaa = Nle
<221> NAME/KEY: MOD_RES
<222> LOCATION: 14, 19
<223> OTHER INFORMATION: Cys at positions 14 and 19 are circularized
<220> FEATURE:
<223> OTHER INFORMATION: Synthetic

<400> SEQUENCE: 40

Ser Ser Ser Ser Ser Ser Ser Ser Ser Ser Xaa Tyr Ser Cys Phe Trp
1               5                   10                  15

Lys Thr Cys Thr
            20

<210> SEQ ID NO 41
<211> LENGTH: 12
<212> TYPE: PRT
<213> ORGANISM: Artificial Sequence
<220> FEATURE:
<221> NAME/KEY: VARIANT
<222> LOCATION: 1
<223> OTHER INFORMATION: Xaa = Sar
<221> NAME/KEY: VARIANT
<222> LOCATION: 3
<223> OTHER INFORMATION: Xaa = Nle
<220> FEATURE:
<223> OTHER INFORMATION: Synthetic

<400> SEQUENCE: 41

Xaa Ser Xaa Tyr Ser Cys Phe Trp Lys Thr Cys Thr
1               5                   10

<210> SEQ ID NO 42
<211> LENGTH: 15
<212> TYPE: PRT
<213> ORGANISM: Artificial Sequence
<220> FEATURE:
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 42

Ser Ser Ser Ser Ser Lys Ser Ser Cys Phe Trp Lys Thr Cys Thr
1               5                   10                  15
```

```
<210> SEQ ID NO 43
<211> LENGTH: 25
<212> TYPE: PRT
<213> ORGANISM: Artificial Sequence
<220> FEATURE:
<221> NAME/KEY: MOD_RES
<222> LOCATION: 19, 24
<223> OTHER INFORMATION: Cys at positions 19 and 24 are circularized
<220> FEATURE:
<223> OTHER INFORMATION: Synthetic

<400> SEQUENCE: 43

Ser Ser Ser Ser Ser Ser Ser Ser Ser Ser Ser Ser Ser Ser Ser Lys
1               5                   10                  15

Tyr Tyr Cys Phe Trp Lys Thr Cys Thr
            20                  25

<210> SEQ ID NO 44
<211> LENGTH: 30
<212> TYPE: PRT
<213> ORGANISM: Artificial Sequence
<220> FEATURE:
<221> NAME/KEY: MOD_RES
<222> LOCATION: 24, 29
<223> OTHER INFORMATION: Cys at positions 24 and 29 are circularized
<220> FEATURE:
<223> OTHER INFORMATION: Synthetic

<400> SEQUENCE: 44

Ser Ser Ser Ser Ser Ser Ser Ser Ser Ser Ser Ser Ser Ser Ser Ser
1               5                   10                  15

Ser Ser Ser Ser Lys Tyr Tyr Cys Phe Trp Lys Thr Cys Thr
            20                  25                  30

<210> SEQ ID NO 45
<211> LENGTH: 20
<212> TYPE: PRT
<213> ORGANISM: Artificial Sequence
<220> FEATURE:
<221> NAME/KEY: MOD_RES
<222> LOCATION: 14, 19
<223> OTHER INFORMATION: Cys at positions 14 and 19 are circularized
<220> FEATURE:
<223> OTHER INFORMATION: Synthetic

<400> SEQUENCE: 45

Gln Gln Gln Gln Gln Gln Gln Gln Gln Gln Lys Tyr Tyr Cys Phe Trp
1               5                   10                  15

Lys Thr Cys Thr
            20

<210> SEQ ID NO 46
<211> LENGTH: 25
<212> TYPE: PRT
<213> ORGANISM: Artificial Sequence
<220> FEATURE:
<221> NAME/KEY: MOD_RES
<222> LOCATION: 19, 24
<223> OTHER INFORMATION: Cys at positions 19 and 24 are circularized
<220> FEATURE:
<223> OTHER INFORMATION: Synthetic

<400> SEQUENCE: 46

Ser Ser Ser Ser Ser Ser Ser Ser Ser Ser Ser Ser Ser Ser Ser Lys
1               5                   10                  15

Tyr Tyr Cys Phe Trp Lys Thr Cys Thr
```

20                25

<210> SEQ ID NO 47
<211> LENGTH: 15
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = 4Pal
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 47

Ser Ser Ser Ser Ser Xaa Tyr Ser Cys Phe Trp Lys Thr Cys Thr
1               5                   10                  15

<210> SEQ ID NO 48
<211> LENGTH: 15
<212> TYPE: PRT
<213> ORGANISM: Artificial Sequence
<220> FEATURE:
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 48

Ser Ser Ser Ser Ser Gln Tyr Ser Cys Phe Trp Lys Thr Cys Thr
1               5                   10                  15

<210> SEQ ID NO 49
<211> LENGTH: 15
<212> TYPE: PRT
<213> ORGANISM: Artificial Sequence
<220> FEATURE:
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 49

Ser Ser Ser Ser Ser Asp Tyr Ser Cys Phe Trp Lys Thr Cys Thr
1               5                   10                  15

<210> SEQ ID NO 50
<211> LENGTH: 16
<212> TYPE: PRT
<213> ORGANISM: Artificial Sequence
<220> FEATURE:
<221> NAME/KEY: VARIANT
<222> LOCATION: 7
<223> OTHER INFORMATION: Xaa = Nle
<221> NAME/KEY: MOD_RES
<222> LOCATION: 10, 15
<223> OTHER INFORMATION: Cys at positions 10 and 15 are circularized
<220> FEATURE:
<223> OTHER INFORMATION: Synthetic

<400> SEQUENCE: 50

Asp Ser Ser Ser Ser Ser Xaa Tyr Ser Cys Phe Trp Lys Thr Cys Thr
1               5                   10                  15

<210> SEQ ID NO 51
<211> LENGTH: 15

```
<212> TYPE: PRT
<213> ORGANISM: Artificial Sequence
<220> FEATURE:
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 51

Ser Ser Ser Ser Ser Ser Tyr Ser Cys Phe Trp Lys Thr Cys Thr
1               5                   10                  15

<210> SEQ ID NO 52
<211> LENGTH: 15
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = Abu
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 52

Ser Ser Ser Ser Ser Xaa Tyr Ser Cys Phe Trp Lys Thr Cys Thr
1               5                   10                  15

<210> SEQ ID NO 53
<211> LENGTH: 15
<212> TYPE: PRT
<213> ORGANISM: Artificial Sequence
<220> FEATURE:
<221> NAME/KEY: MOD_RES
<222> LOCATION: 9, 14
<223> OTHER INFORMATION: Cys at positions 9 and 14 are circularized
<220> FEATURE:
<223> OTHER INFORMATION: Synthetic

<400> SEQUENCE: 53

Ser Ser Ser Ser Ser Thr Tyr Ser Cys Phe Trp Lys Thr Cys Thr
1               5                   10                  15

<210> SEQ ID NO 54
<211> LENGTH: 16
<212> TYPE: PRT
<213> ORGANISM: Artificial Sequence
<220> FEATURE:
<221> NAME/KEY: MOD_RES
<222> LOCATION: 10, 15
<223> OTHER INFORMATION: Cys at positions 10 and 15 are circularized
<220> FEATURE:
<223> OTHER INFORMATION: Synthetic

<400> SEQUENCE: 54

Asp Ser Ser Ser Ser Ser Thr Tyr Ser Cys Phe Trp Lys Thr Cys Thr
1               5                   10                  15

<210> SEQ ID NO 55
<211> LENGTH: 15
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = hSer
<221> NAME/KEY: MOD_RES
<222> LOCATION: 9, 14
```

<223> OTHER INFORMATION: Cys at position 9 and 14 are circularized
<220> FEATURE:
<223> OTHER INFORMATION: Synthetic

<400> SEQUENCE: 55

Ser Ser Ser Ser Ser Xaa Tyr Ser Cys Phe Trp Lys Thr Cys Thr
1               5                   10                  15

<210> SEQ ID NO 56
<211> LENGTH: 18
<212> TYPE: PRT
<213> ORGANISM: Artificial Sequence
<220> FEATURE:
<221> NAME/KEY: VARIANT
<222> LOCATION: 9
<223> OTHER INFORMATION: Xaa = 4Pal
<221> NAME/KEY: MOD_RES
<222> LOCATION: 12, 17
<223> OTHER INFORMATION: Cys at positions 12 and 17 are circularized
<220> FEATURE:
<223> OTHER INFORMATION: Synthetic

<400> SEQUENCE: 56

Gly Gly Asp Ser Ser Ser Ser Xaa Tyr Ser Cys Phe Trp Lys Thr
1               5                   10                  15

Cys Thr

<210> SEQ ID NO 57
<211> LENGTH: 22
<212> TYPE: PRT
<213> ORGANISM: Artificial Sequence
<220> FEATURE:
<221> NAME/KEY: VARIANT
<222> LOCATION: 13
<223> OTHER INFORMATION: Xaa = Nva
<221> NAME/KEY: MOD_RES
<222> LOCATION: 16, 21
<223> OTHER INFORMATION: Cys at positions 16 and 21 are circularized
<220> FEATURE:
<223> OTHER INFORMATION: Synthetic

<400> SEQUENCE: 57

Ser Ser Ser Gln Ser Ser Ser Gln Ser Ser Ser Gln Xaa Tyr Ser Cys
1               5                   10                  15

Phe Trp Lys Thr Cys Thr
                20

<210> SEQ ID NO 58
<211> LENGTH: 19
<212> TYPE: PRT
<213> ORGANISM: Artificial Sequence
<220> FEATURE:
<221> NAME/KEY: VARIANT
<222> LOCATION: 10
<223> OTHER INFORMATION: Xaa =Abu
<221> NAME/KEY: MOD_RES
<222> LOCATION: 13, 18
<223> OTHER INFORMATION: Cys at positions 13 and 18 are circularized
<220> FEATURE:
<223> OTHER INFORMATION: Synthetic

<400> SEQUENCE: 58

Ser Ser Ser Ser Ser Ser Ser Ser Ser Xaa Tyr Ser Cys Phe Trp Lys
1               5                   10                  15

Thr Cys Thr